(12) United States Patent
Aumer et al.

(10) Patent No.: US 9,794,653 B2
(45) Date of Patent: Oct. 17, 2017

(54) METHODS AND APPARATUS FOR IMPROVING SIGNAL QUALITY IN WEARABLE BIOMETRIC MONITORING DEVICES

(71) Applicant: Valencell, Inc., Raleigh, NC (US)

(72) Inventors: Michael Edward Aumer, Raleigh, NC (US); Steven Francis LeBoeuf, Raleigh, NC (US)

(73) Assignee: Valencell, Inc., Raleigh, NC (US)

( * ) Notice: Subject to any disclaimer, the term of this patent is extended or adjusted under 35 U.S.C. 154(b) by 0 days.

(21) Appl. No.: 14/829,032

(22) Filed: Aug. 18, 2015

(65) Prior Publication Data

US 2016/0094899 A1  Mar. 31, 2016

Related U.S. Application Data

(60) Provisional application No. 62/056,510, filed on Sep. 27, 2014, provisional application No. 62/110,655, filed on Feb. 2, 2015.

(51) Int. Cl.
*H04Q 9/00* (2006.01)
*G08B 21/18* (2006.01)
(Continued)

(52) U.S. Cl.
CPC ............ *H04Q 9/00* (2013.01); *A61B 5/6802* (2013.01); *G08B 21/18* (2013.01); *H04R 1/1091* (2013.01);
(Continued)

(58) Field of Classification Search
CPC ........ H04Q 9/00; A61B 5/6802; G08B 21/18; H04R 1/1091
(Continued)

(56) References Cited

U.S. PATENT DOCUMENTS 3,595,219 A   7/1971  Friedlander et al.
4,240,882 A  12/1980  Ang et al.
(Continued)

FOREIGN PATENT DOCUMENTS

CN   101212927 A   7/2008
CN   201438747 U   4/2010
(Continued)

OTHER PUBLICATIONS

Edmison et al., "E-Textile Based Automatic Activity Diary for Medical Annotation and Analysis," Proc. BSN 2006 Int. Workshop Wearable Implantable Body Sensor Netw. (2006), pp. 131-145, Apr. 3-5, 2006.
(Continued)

*Primary Examiner* — Joseph Feild
*Assistant Examiner* — Omar Casillashernandez
(74) *Attorney, Agent, or Firm* — Myers Bigel, P.A.

(57) ABSTRACT

A wearable biometric monitoring device is configured to assess the biometric signal quality of one or more sensors associated with the monitoring device, determine how the user should adjust the device to improve the biometric fit, and instruct the user to wear the biometric monitoring device a certain way. Communicating instructions to a user may include instructing the user to execute a testing regimen while wearing the biometric monitoring device. The testing regimen facilitates an estimation of a signal quality that can be used to provide feedback to the user that he/she needs to adjust the device to improve the biometric fit and the biometric signal quality.

17 Claims, 14 Drawing Sheets

(51) Int. Cl.
*H04R 1/10* (2006.01)
*A61B 5/00* (2006.01)
*A61B 5/024* (2006.01)
*A61B 5/11* (2006.01)
*A61B 5/1455* (2006.01)

(52) U.S. Cl.
CPC ......... *A61B 5/02405* (2013.01); *A61B 5/1118* (2013.01); *A61B 5/14551* (2013.01); *A61B 5/7221* (2013.01); *H04R 1/1008* (2013.01); *H04R 1/1016* (2013.01)

(58) Field of Classification Search
USPC .................................................. 340/870.07
See application file for complete search history.

(56) References Cited

U.S. PATENT DOCUMENTS

| | | |
|---|---|---|
| 4,331,154 A | 5/1982 | Broadwater et al. |
| 4,438,772 A | 3/1984 | Slavin |
| 4,491,760 A | 1/1985 | Linvill |
| 4,521,499 A | 6/1985 | Switzer |
| 4,541,905 A | 9/1985 | Kuwana et al. |
| 4,592,807 A | 6/1986 | Switzer |
| 4,655,225 A | 4/1987 | Dahne et al. |
| 4,830,014 A | 5/1989 | Goodman et al. |
| 4,882,492 A | 11/1989 | Schlager |
| 4,896,676 A | 1/1990 | Sasaki |
| 4,928,704 A | 5/1990 | Hardt |
| 4,957,109 A | 9/1990 | Groeger et al. |
| 5,002,060 A | 3/1991 | Nedivi |
| 5,022,970 A | 6/1991 | Cook et al. |
| 5,025,791 A | 6/1991 | Niwa |
| 5,079,421 A | 1/1992 | Knudson et al. |
| 5,080,098 A | 1/1992 | Willett et al. |
| 5,086,229 A | 2/1992 | Rosenthal et al. |
| 5,143,078 A | 9/1992 | Mather et al. |
| 5,226,417 A | 7/1993 | Swedlow et al. |
| 5,237,994 A | 8/1993 | Goldberger |
| 5,348,002 A | 9/1994 | Caro |
| 5,377,100 A | 12/1994 | Pope et al. |
| 5,482,036 A | 1/1996 | Diab et al. |
| 5,492,129 A | 2/1996 | Greenberger |
| 5,499,301 A | 3/1996 | Sudo et al. |
| 5,581,648 A | 12/1996 | Sahagen |
| 5,596,987 A | 1/1997 | Chance |
| 5,662,117 A | 9/1997 | Bittman |
| 5,673,692 A | 10/1997 | Schulze et al. |
| 5,697,374 A | 12/1997 | Odagiri et al. |
| 5,711,308 A | 1/1998 | Singer |
| 5,725,480 A | 3/1998 | Oosta et al. |
| 5,743,260 A | 4/1998 | Chung et al. |
| 5,779,631 A | 7/1998 | Chance |
| 5,797,841 A | 8/1998 | Delonzor et al. |
| 5,807,114 A | 9/1998 | Hodges et al. |
| 5,807,267 A | 9/1998 | Bryars et al. |
| 5,853,005 A | 12/1998 | Scanlon |
| 5,904,654 A | 5/1999 | Wohltmann et al. |
| 5,938,593 A | 8/1999 | Quellette |
| 5,964,701 A | 10/1999 | Asada et al. |
| 5,971,931 A | 10/1999 | Raff |
| 5,974,338 A | 10/1999 | Asano et al. |
| 5,995,858 A | 11/1999 | Kinast |
| 6,004,274 A | 12/1999 | Nolan et al. |
| 6,013,007 A | 1/2000 | Root et al. |
| 6,023,541 A | 2/2000 | Merchant et al. |
| 6,030,342 A | 2/2000 | Amano et al. |
| 6,045,511 A | 4/2000 | Ott et al. |
| 6,067,006 A | 5/2000 | O'Brien |
| 6,070,093 A | 5/2000 | Oosta et al. |
| 6,078,829 A | 6/2000 | Uchida et al. |
| 6,080,110 A | 6/2000 | Thorgersen |
| 6,081,742 A | 6/2000 | Amano et al. |
| 6,186,145 B1 | 2/2001 | Brown |
| 6,198,394 B1 | 3/2001 | Jacobsen et al. |
| 6,198,951 B1 | 3/2001 | Kosuda et al. |
| 6,205,354 B1 | 3/2001 | Gellermann et al. |
| 6,231,519 B1 | 5/2001 | Blants et al. |
| 6,283,915 B1 | 9/2001 | Aceti et al. |
| 6,285,816 B1 | 9/2001 | Anderson et al. |
| 6,289,230 B1 | 9/2001 | Chaiken et al. |
| 6,298,314 B1 | 10/2001 | Blackadar et al. |
| 6,332,868 B1 | 12/2001 | Sato et al. |
| 6,358,216 B1 | 3/2002 | Kraus et al. |
| 6,361,660 B1 | 3/2002 | Goldstein |
| 6,371,925 B1 | 4/2002 | Imai et al. |
| 6,374,129 B1 | 4/2002 | Chin et al. |
| 6,415,167 B1 | 7/2002 | Blank et al. |
| 6,443,890 B1 | 9/2002 | Schulze et al. |
| 6,444,474 B1 | 9/2002 | Thomas et al. |
| 6,454,718 B1 | 9/2002 | Clift |
| 6,458,080 B1 | 10/2002 | Brown et al. |
| 6,470,893 B1 | 10/2002 | Boesen |
| 6,513,532 B2 | 2/2003 | Mault et al. |
| 6,514,278 B1 | 2/2003 | Hibst et al. |
| 6,527,711 B1 | 3/2003 | Stivoric et al. |
| 6,527,712 B1 | 3/2003 | Brown et al. |
| 6,529,754 B2 | 3/2003 | Kondo |
| 6,534,012 B1 | 3/2003 | Hazen et al. |
| 6,556,852 B1 | 4/2003 | Schulze et al. |
| 6,569,094 B2 | 5/2003 | Suzuki et al. |
| 6,571,117 B1 | 5/2003 | Marbach |
| 6,605,038 B1 | 8/2003 | Teller et al. |
| 6,616,613 B1 | 9/2003 | Goodman |
| 6,631,196 B1 | 10/2003 | Taenzer et al. |
| 6,647,378 B2 | 11/2003 | Kindo |
| 6,656,116 B2 | 12/2003 | Kim et al. |
| 6,694,180 B1 | 2/2004 | Boesen |
| 6,745,061 B1 | 6/2004 | Hicks et al. |
| 6,748,254 B2 | 6/2004 | O'Neil et al. |
| 6,760,610 B2 | 7/2004 | Tschupp et al. |
| 6,783,501 B2 | 8/2004 | Takahashi et al. |
| 6,808,473 B2 | 10/2004 | Hisano et al. |
| 6,859,658 B1 | 2/2005 | Krug |
| 6,893,396 B2 | 5/2005 | Schulze et al. |
| 6,941,239 B2 | 9/2005 | Unuma et al. |
| 6,953,435 B2 | 10/2005 | Kondo et al. |
| 6,996,427 B2 | 2/2006 | Ali et al. |
| 6,997,879 B1 | 2/2006 | Turcott |
| 7,018,338 B2 | 3/2006 | Vetter et al. |
| 7,024,369 B1 | 4/2006 | Brown et al. |
| 7,030,359 B2 | 4/2006 | Römhild |
| 7,034,694 B2 | 4/2006 | Yamaguchi et al. |
| 7,041,062 B2 | 5/2006 | Friedrichs et al. |
| 7,043,287 B1 | 5/2006 | Khalil et al. |
| 7,054,674 B2 | 5/2006 | Cane et al. |
| 7,088,234 B2 | 8/2006 | Naito et al. |
| 7,107,088 B2 | 9/2006 | Aceti |
| 7,113,815 B2 | 9/2006 | O'Neil et al. |
| 7,117,032 B2 | 10/2006 | Childre et al. |
| 7,163,512 B1 | 1/2007 | Childre et al. |
| 7,175,601 B2 | 2/2007 | Verjus et al. |
| 7,209,775 B2 | 4/2007 | Bae et al. |
| 7,217,224 B2 | 5/2007 | Thomas |
| 7,252,639 B2 | 8/2007 | Kimura et al. |
| 7,263,396 B2 | 8/2007 | Chen et al. |
| 7,289,837 B2 | 10/2007 | Mannheimer et al. |
| 7,336,982 B2 | 2/2008 | Yoo et al. |
| 7,341,559 B2 | 3/2008 | Schultz et al. |
| 7,376,451 B2 | 5/2008 | Mahony et al. |
| 7,470,234 B1 | 12/2008 | Elhag et al. |
| 7,483,730 B2 | 1/2009 | Diab et al. |
| 7,486,988 B2 | 2/2009 | Goodall et al. |
| 7,507,207 B2 | 3/2009 | Sakai et al. |
| 7,519,327 B2 | 4/2009 | White |
| 7,526,327 B2 | 4/2009 | Blondeau et al. |
| 7,583,994 B2 | 9/2009 | Scholz |
| 7,625,285 B2 | 12/2009 | Breving |
| 7,652,569 B2 | 1/2010 | Kiff et al. |
| 7,689,437 B1 | 3/2010 | Teller et al. |
| 7,695,440 B2 | 4/2010 | Kondo et al. |
| 7,725,147 B2 | 5/2010 | Li et al. |
| 7,756,559 B2 | 7/2010 | Abreu |
| 7,843,325 B2 | 11/2010 | Otto |

(56) References Cited

U.S. PATENT DOCUMENTS

| | | |
|---|---|---|
| 7,894,869 B2 | 2/2011 | Hoarau |
| 7,914,468 B2 | 3/2011 | Shalon et al. |
| 7,991,448 B2 | 8/2011 | Edgar et al. |
| 7,998,079 B2 | 8/2011 | Nagai et al. |
| 8,050,728 B2 | 11/2011 | Al-Ali et al. |
| 8,055,319 B2 | 11/2011 | Oh et al. |
| 8,055,330 B2 | 11/2011 | Egozi |
| 8,059,924 B1 | 11/2011 | Letant et al. |
| 8,130,105 B2 | 3/2012 | Al-Ali et al. |
| 8,137,270 B2 | 3/2012 | Keenan et al. |
| 8,157,730 B2 | 4/2012 | LeBoeuf et al. |
| 8,172,459 B2 | 5/2012 | Abreu |
| 8,175,670 B2 | 5/2012 | Baker, Jr. et al. |
| 8,204,730 B2 | 6/2012 | Liu et al. |
| 8,204,786 B2 | 6/2012 | LeBoeuf et al. |
| 8,233,955 B2 | 7/2012 | Al-Ali et al. |
| 8,251,903 B2 | 8/2012 | LeBoeuf et al. |
| 8,255,027 B2 | 8/2012 | Al-Ali et al. |
| 8,255,029 B2 | 8/2012 | Addison et al. |
| 8,303,512 B2 | 11/2012 | Kosuda et al. |
| 8,320,982 B2 | 11/2012 | LeBoeuf et al. |
| 8,323,982 B2 | 12/2012 | LeBoeuf et al. |
| 8,328,420 B2 | 12/2012 | Abreu |
| 8,416,959 B2 | 4/2013 | Lott et al. |
| 8,491,492 B2 | 7/2013 | Shinar et al. |
| 8,504,679 B2 | 8/2013 | Spire et al. |
| 8,506,524 B2 | 8/2013 | Graskov et al. |
| 8,512,242 B2 | 8/2013 | LeBoeuf et al. |
| 8,647,270 B2 | 2/2014 | LeBoeuf et al. |
| 8,652,040 B2 | 2/2014 | LeBoeuf et al. |
| 8,652,409 B2 | 2/2014 | LeBoeuf et al. |
| 8,679,008 B2 | 3/2014 | Hughes et al. |
| 8,700,111 B2 | 4/2014 | LeBoeuf et al. |
| 8,702,607 B2 | 4/2014 | LeBoeuf et al. |
| 8,730,048 B2 | 5/2014 | Shen et al. |
| 8,788,002 B2 | 7/2014 | LeBoeuf et al. |
| 8,886,269 B2 | 11/2014 | LeBoeuf et al. |
| 8,888,701 B2 | 11/2014 | LeBoeuf et al. |
| 8,923,941 B2 | 12/2014 | LeBoeuf et al. |
| 8,929,965 B2 | 1/2015 | LeBoeuf et al. |
| 8,929,966 B2 | 1/2015 | LeBoeuf et al. |
| 8,934,952 B2 | 1/2015 | LeBoeuf et al. |
| 8,942,776 B2 | 1/2015 | LeBoeuf et al. |
| 8,961,415 B2 | 2/2015 | LeBoeuf et al. |
| 9,005,129 B2 | 4/2015 | Venkatraman et al. |
| 2001/0049471 A1 | 12/2001 | Suzuki et al. |
| 2002/0035340 A1 | 3/2002 | Fraden et al. |
| 2002/0143242 A1 | 10/2002 | Nemirovski |
| 2002/0156386 A1 | 10/2002 | Dardik et al. |
| 2002/0156654 A1 | 10/2002 | Roe et al. |
| 2002/0186137 A1 | 12/2002 | Skardon |
| 2002/0188210 A1 | 12/2002 | Aizawa |
| 2002/0194002 A1 | 12/2002 | Petrushin |
| 2003/0002705 A1 | 1/2003 | Boesen |
| 2003/0007631 A1 | 1/2003 | Bolognesi et al. |
| 2003/0045785 A1 | 3/2003 | Diab et al. |
| 2003/0050563 A1 | 3/2003 | Suribhotla et al. |
| 2003/0064712 A1 | 4/2003 | Gaston et al. |
| 2003/0065257 A1 | 4/2003 | Mault et al. |
| 2003/0083583 A1 | 5/2003 | Kovtun et al. |
| 2003/0109030 A1 | 6/2003 | Uchida et al. |
| 2003/0181795 A1 | 9/2003 | Suzuki et al. |
| 2003/0212336 A1* | 11/2003 | Lee ............... A61B 5/02416 600/504 |
| 2003/0220584 A1 | 11/2003 | Honeyager et al. |
| 2003/0222268 A1 | 12/2003 | Yocom et al. |
| 2004/0004547 A1 | 1/2004 | Appelt et al. |
| 2004/0022700 A1 | 2/2004 | Kim et al. |
| 2004/0030581 A1 | 2/2004 | Leven |
| 2004/0034289 A1 | 2/2004 | Teller et al. |
| 2004/0034293 A1 | 2/2004 | Kimball |
| 2004/0054291 A1 | 3/2004 | Schulz et al. |
| 2004/0075677 A1 | 4/2004 | Loyall et al. |
| 2004/0077934 A1 | 4/2004 | Massad |
| 2004/0082842 A1 | 4/2004 | Lumba et al. |
| 2004/0103146 A1 | 5/2004 | Park |
| 2004/0117204 A1 | 6/2004 | Mazar et al. |
| 2004/0120844 A1 | 6/2004 | Tribelsky et al. |
| 2004/0122294 A1 | 6/2004 | Hatlestad et al. |
| 2004/0122702 A1 | 6/2004 | Sabol et al. |
| 2004/0133123 A1 | 7/2004 | Leonhardt et al. |
| 2004/0135571 A1 | 7/2004 | Uutela et al. |
| 2004/0138578 A1 | 7/2004 | Pineda et al. |
| 2004/0186390 A1 | 9/2004 | Ross et al. |
| 2004/0219056 A1 | 11/2004 | Tribelsky et al. |
| 2004/0220488 A1 | 11/2004 | Vyshedskiy et al. |
| 2004/0225207 A1 | 11/2004 | Bae et al. |
| 2004/0228494 A1 | 11/2004 | Smith |
| 2004/0242976 A1 | 12/2004 | Abreu |
| 2005/0004458 A1 | 1/2005 | Kanayama et al. |
| 2005/0027216 A1 | 2/2005 | Guillemaud et al. |
| 2005/0030540 A1 | 2/2005 | Thornton |
| 2005/0033200 A1 | 2/2005 | Soehren et al. |
| 2005/0038349 A1 | 2/2005 | Choi et al. |
| 2005/0043600 A1 | 2/2005 | Diab et al. |
| 2005/0043630 A1 | 2/2005 | Buchert et al. |
| 2005/0058456 A1 | 3/2005 | Yoo |
| 2005/0059870 A1 | 3/2005 | Aceti |
| 2005/0070809 A1* | 3/2005 | Acres ............... A61B 5/0006 600/508 |
| 2005/0084666 A1 | 4/2005 | Pong et al. |
| 2005/0101845 A1 | 5/2005 | Nihtila |
| 2005/0101872 A1 | 5/2005 | Sattler et al. |
| 2005/0113167 A1 | 5/2005 | Buchner et al. |
| 2005/0113656 A1 | 5/2005 | Chance |
| 2005/0113703 A1 | 5/2005 | Farringdon et al. |
| 2005/0116820 A1 | 6/2005 | Goldreich |
| 2005/0119833 A1 | 6/2005 | Nanikashvili |
| 2005/0148883 A1 | 7/2005 | Boesen |
| 2005/0154264 A1 | 7/2005 | Lecompte et al. |
| 2005/0177034 A1 | 8/2005 | Beaumont |
| 2005/0187448 A1 | 8/2005 | Petersen et al. |
| 2005/0187453 A1 | 8/2005 | Petersen et al. |
| 2005/0192515 A1 | 9/2005 | Givens et al. |
| 2005/0196009 A1 | 9/2005 | Boesen |
| 2005/0203349 A1 | 9/2005 | Nanikashvili |
| 2005/0203357 A1 | 9/2005 | Debreczeny et al. |
| 2005/0209516 A1 | 9/2005 | Fraden |
| 2005/0222487 A1 | 10/2005 | Miller et al. |
| 2005/0222903 A1 | 10/2005 | Buchheit et al. |
| 2005/0228244 A1 | 10/2005 | Banet |
| 2005/0228299 A1 | 10/2005 | Banet |
| 2005/0240087 A1 | 10/2005 | Keenan et al. |
| 2005/0258816 A1 | 11/2005 | Zen et al. |
| 2005/0259811 A1 | 11/2005 | Kimm et al. |
| 2006/0009685 A1 | 1/2006 | Finarov et al. |
| 2006/0012567 A1 | 1/2006 | Sicklinger |
| 2006/0063993 A1 | 3/2006 | Yu et al. |
| 2006/0064037 A1 | 3/2006 | Shalon et al. |
| 2006/0084878 A1 | 4/2006 | Banet et al. |
| 2006/0084879 A1 | 4/2006 | Nazarian et al. |
| 2006/0122520 A1 | 6/2006 | Banet et al. |
| 2006/0123885 A1 | 6/2006 | Yates et al. |
| 2006/0140425 A1 | 6/2006 | Berg et al. |
| 2006/0142665 A1 | 6/2006 | Garay et al. |
| 2006/0202816 A1 | 9/2006 | Crump et al. |
| 2006/0205083 A1 | 9/2006 | Zhao |
| 2006/0210058 A1 | 9/2006 | Kock et al. |
| 2006/0211922 A1 | 9/2006 | Al-Ali et al. |
| 2006/0211924 A1 | 9/2006 | Dalke et al. |
| 2006/0217598 A1 | 9/2006 | Miyajima et al. |
| 2006/0224059 A1 | 10/2006 | Swedlow et al. |
| 2006/0240558 A1 | 10/2006 | Zhao |
| 2006/0246342 A1 | 11/2006 | MacPhee |
| 2006/0251277 A1 | 11/2006 | Cho |
| 2006/0251334 A1 | 11/2006 | Oba et al. |
| 2006/0252999 A1 | 11/2006 | Devaul et al. |
| 2006/0264730 A1 | 11/2006 | Stivoric et al. |
| 2006/0292533 A1 | 12/2006 | Selod |
| 2006/0293921 A1 | 12/2006 | McCarthy et al. |
| 2007/0004449 A1 | 1/2007 | Sham |
| 2007/0004969 A1 | 1/2007 | Kong et al. |
| 2007/0015992 A1 | 1/2007 | Filkins et al. |
| 2007/0021206 A1 | 1/2007 | Sunnen |

(56) References Cited

U.S. PATENT DOCUMENTS

| | | |
|---|---|---|
| 2007/0027367 A1 | 2/2007 | Oliver et al. |
| 2007/0027399 A1 | 2/2007 | Chou |
| 2007/0036383 A1 | 2/2007 | Romero |
| 2007/0050215 A1 | 3/2007 | Kil et al. |
| 2007/0060800 A1 | 3/2007 | Drinan et al. |
| 2007/0063850 A1 | 3/2007 | Devaul et al. |
| 2007/0082789 A1 | 4/2007 | Nissila et al. |
| 2007/0083092 A1 | 4/2007 | Rippo et al. |
| 2007/0083095 A1 | 4/2007 | Rippo et al. |
| 2007/0088221 A1 | 4/2007 | Stahmann |
| 2007/0093702 A1 | 4/2007 | Yu et al. |
| 2007/0106167 A1 | 5/2007 | Kinast |
| 2007/0112273 A1 | 5/2007 | Rogers |
| 2007/0112598 A1 | 5/2007 | Heckerman et al. |
| 2007/0116314 A1 | 5/2007 | Grilliot et al. |
| 2007/0118043 A1 | 5/2007 | Oliver et al. |
| 2007/0165872 A1 | 7/2007 | Bridger et al. |
| 2007/0167850 A1 | 7/2007 | Russell et al. |
| 2007/0191718 A1 | 8/2007 | Nakamura |
| 2007/0197878 A1 | 8/2007 | Shklarski |
| 2007/0197881 A1 | 8/2007 | Wolf et al. |
| 2007/0213020 A1 | 9/2007 | Novac |
| 2007/0230714 A1 | 10/2007 | Armstrong |
| 2007/0233403 A1 | 10/2007 | Alwan et al. |
| 2007/0265097 A1 | 11/2007 | Havukainen |
| 2007/0270667 A1 | 11/2007 | Coppi et al. |
| 2007/0270671 A1 | 11/2007 | Gal |
| 2007/0293781 A1 | 12/2007 | Sims et al. |
| 2007/0299330 A1 | 12/2007 | Couronne et al. |
| 2008/0004536 A1 | 1/2008 | Baxi et al. |
| 2008/0015424 A1 | 1/2008 | Bernreuter |
| 2008/0039731 A1 | 2/2008 | McCombie et al. |
| 2008/0076972 A1 | 3/2008 | Dorogusker et al. |
| 2008/0081963 A1 | 4/2008 | Naghavi et al. |
| 2008/0086533 A1 | 4/2008 | Neuhauser et al. |
| 2008/0096726 A1 | 4/2008 | Riley et al. |
| 2008/0114220 A1 | 5/2008 | Banet et al. |
| 2008/0132798 A1 | 6/2008 | Hong et al. |
| 2008/0141301 A1 | 6/2008 | Azzaro et al. |
| 2008/0154098 A1 | 6/2008 | Morris et al. |
| 2008/0154105 A1 | 6/2008 | Lemay |
| 2008/0165017 A1 | 7/2008 | Schwartz |
| 2008/0170600 A1 | 7/2008 | Sattler et al. |
| 2008/0171945 A1 | 7/2008 | Dotter |
| 2008/0177162 A1 | 7/2008 | Bae et al. |
| 2008/0200774 A1 | 8/2008 | Luo |
| 2008/0203144 A1 | 8/2008 | Kim |
| 2008/0221461 A1 | 9/2008 | Zhou et al. |
| 2008/0249594 A1 | 10/2008 | Dietrich |
| 2008/0287752 A1 | 11/2008 | Stroetz et al. |
| 2009/0005662 A1 | 1/2009 | Petersen et al. |
| 2009/0006457 A1 | 1/2009 | Stivoric et al. |
| 2009/0010461 A1 | 1/2009 | Klinghult et al. |
| 2009/0030350 A1 | 1/2009 | Yang et al. |
| 2009/0054751 A1 | 2/2009 | Babashan et al. |
| 2009/0054752 A1 | 2/2009 | Jonnalagadda et al. |
| 2009/0069645 A1 | 3/2009 | Nielsen et al. |
| 2009/0082994 A1 | 3/2009 | Schuler et al. |
| 2009/0088611 A1 | 4/2009 | Buschmann |
| 2009/0093687 A1 | 4/2009 | Telfort et al. |
| 2009/0105548 A1 | 4/2009 | Bart |
| 2009/0105556 A1 | 4/2009 | Fricke et al. |
| 2009/0112111 A1 | 4/2009 | Shimizu et al. |
| 2009/0131761 A1 | 5/2009 | Moroney, III et al. |
| 2009/0131764 A1 | 5/2009 | Lee et al. |
| 2009/0175456 A1 | 7/2009 | Johnson |
| 2009/0177097 A1 | 7/2009 | Ma et al. |
| 2009/0214060 A1 | 8/2009 | Chuang et al. |
| 2009/0221888 A1 | 9/2009 | Wijesiriwardana |
| 2009/0227853 A1 | 9/2009 | Wijesiriwardana |
| 2009/0240125 A1 | 9/2009 | Such et al. |
| 2009/0253992 A1 | 10/2009 | Van Der Loo |
| 2009/0253996 A1 | 10/2009 | Lee et al. |
| 2009/0264711 A1 | 10/2009 | Schuler et al. |
| 2009/0270698 A1 | 10/2009 | Shioi et al. |
| 2009/0287067 A1 | 11/2009 | Dorogusker et al. |
| 2009/0299215 A1 | 12/2009 | Zhang |
| 2010/0004517 A1 | 1/2010 | Bryenton et al. |
| 2010/0022861 A1 | 1/2010 | Cinbis et al. |
| 2010/0045663 A1 | 2/2010 | Chen et al. |
| 2010/0100013 A1 | 4/2010 | Hu et al. |
| 2010/0113948 A1 | 5/2010 | Yang et al. |
| 2010/0168531 A1 | 7/2010 | Shaltis et al. |
| 2010/0172522 A1 | 7/2010 | Mooring et al. |
| 2010/0179389 A1 | 7/2010 | Moroney et al. |
| 2010/0185105 A1 | 7/2010 | Baldinger |
| 2010/0217100 A1 | 8/2010 | LeBoeuf |
| 2010/0217103 A1 | 8/2010 | Abdul-Hafiz et al. |
| 2010/0222655 A1 | 9/2010 | Starr et al. |
| 2010/0228315 A1 | 9/2010 | Nielsen |
| 2010/0234714 A1 | 9/2010 | Mercier et al. |
| 2010/0268056 A1 | 10/2010 | Picard et al. |
| 2010/0274100 A1 | 10/2010 | Behar et al. |
| 2010/0274109 A1 | 10/2010 | Hu et al. |
| 2010/0292589 A1 | 11/2010 | Goodman |
| 2010/0298653 A1 | 11/2010 | McCombie et al. |
| 2011/0028810 A1 | 2/2011 | Van Slyke et al. |
| 2011/0028813 A1 | 2/2011 | Watson et al. |
| 2011/0081037 A1 | 4/2011 | Oh et al. |
| 2011/0098112 A1 | 4/2011 | LeBoeuf |
| 2011/0105869 A1 | 5/2011 | Wilson et al. |
| 2011/0112382 A1 | 5/2011 | Li et al. |
| 2011/0130638 A1 | 6/2011 | Raridan, Jr. |
| 2011/0142371 A1 | 6/2011 | King et al. |
| 2011/0288379 A1 | 11/2011 | Wu |
| 2012/0030547 A1 | 2/2012 | Raptis et al. |
| 2012/0095303 A1 | 4/2012 | He |
| 2012/0156933 A1 | 6/2012 | Kreger et al. |
| 2012/0179011 A1 | 7/2012 | Moon et al. |
| 2012/0203081 A1 | 8/2012 | LeBoeuf et al. |
| 2012/0226111 A1 | 9/2012 | LeBoeuf et al. |
| 2012/0226112 A1 | 9/2012 | LeBoeuf et al. |
| 2012/0277548 A1 | 11/2012 | Burton |
| 2012/0283577 A1 | 11/2012 | LeBoeuf et al. |
| 2012/0296184 A1 | 11/2012 | LeBoeuf et al. |
| 2012/0323086 A1 | 12/2012 | Hansen |
| 2013/0053661 A1 | 2/2013 | Alberth et al. |
| 2013/0072765 A1* | 3/2013 | Kahn ............... A61B 5/01 600/301 |
| 2013/0131519 A1* | 5/2013 | LeBoeuf ............ A61B 5/0077 600/476 |
| 2013/0245387 A1 | 9/2013 | Patel |
| 2013/0336495 A1 | 12/2013 | Burgett et al. |
| 2014/0012105 A1 | 1/2014 | LeBoeuf et al. |
| 2014/0051940 A1 | 2/2014 | Messerschmidt |
| 2014/0051948 A1 | 2/2014 | LeBoeuf et al. |
| 2014/0052567 A1 | 2/2014 | Bhardwaj et al. |
| 2014/0058220 A1 | 2/2014 | LeBoeuf et al. |
| 2014/0073486 A1 | 3/2014 | Ahmed et al. |
| 2014/0094663 A1 | 4/2014 | LeBoeuf et al. |
| 2014/0100432 A1 | 4/2014 | Golda et al. |
| 2014/0114147 A1 | 4/2014 | Romesburg et al. |
| 2014/0127996 A1 | 5/2014 | Park et al. |
| 2014/0128690 A1 | 5/2014 | LeBoeuf et al. |
| 2014/0135596 A1 | 5/2014 | LeBoeuf et al. |
| 2014/0140567 A1 | 5/2014 | LeBoeuf et al. |
| 2014/0219467 A1 | 8/2014 | Kurtz |
| 2014/0235967 A1 | 8/2014 | LeBoeuf et al. |
| 2014/0235968 A1 | 8/2014 | LeBoeuf et al. |
| 2014/0236531 A1 | 8/2014 | Carter |
| 2014/0243617 A1 | 8/2014 | LeBoeuf et al. |
| 2014/0243620 A1 | 8/2014 | LeBoeuf et al. |
| 2014/0275850 A1 | 9/2014 | Venkatraman et al. |
| 2014/0275852 A1* | 9/2014 | Hong ............... A61B 5/02427 600/301 |
| 2014/0275855 A1 | 9/2014 | LeBoeuf et al. |
| 2014/0287833 A1 | 9/2014 | LeBoeuf et al. |
| 2014/0288396 A1 | 9/2014 | LeBoeuf et al. |
| 2014/0323829 A1 | 10/2014 | LeBoeuf et al. |
| 2014/0323830 A1 | 10/2014 | LeBoeuf et al. |
| 2014/0323880 A1 | 10/2014 | Ahmed et al. |
| 2014/0378844 A1 | 12/2014 | Fei |
| 2015/0031967 A1 | 1/2015 | LeBoeuf et al. |
| 2015/0032009 A1 | 1/2015 | LeBoeuf et al. |

(56) References Cited

U.S. PATENT DOCUMENTS

| | | | | |
|---|---|---|---|---|
| 2015/0057967 A1* | 2/2015 | Albinali | ............... | A61B 5/681 |
| | | | | 702/150 |
| 2015/0265217 A1* | 9/2015 | Penders | ............... | A61B 5/721 |
| | | | | 600/301 |
| 2015/0289820 A1* | 10/2015 | Miller | ............... | A61B 5/7221 |
| | | | | 600/300 |
| 2015/0342481 A1* | 12/2015 | Liu | ............... | A61B 5/02427 |
| | | | | 600/479 |
| 2016/0022220 A1* | 1/2016 | Lee | ............... | A61B 5/721 |
| | | | | 600/479 |

FOREIGN PATENT DOCUMENTS

| | | |
|---|---|---|
| DE | 3910749 A1 | 10/1990 |
| EP | 1 297 784 A1 | 4/2003 |
| EP | 1 480 278 A2 | 11/2004 |
| EP | 2 077 091 A2 | 7/2009 |
| EP | 2 182 839 B1 | 10/2011 |
| GB | 2 408 209 A | 5/2005 |
| GB | 2 411 719 A | 9/2005 |
| JP | 7-241279 | 9/1995 |
| JP | 9-253062 | 9/1997 |
| JP | 9-299342 | 11/1997 |
| JP | 2000-116611 | 4/2000 |
| JP | 2001-025462 | 1/2001 |
| JP | 2003-159221 | 6/2003 |
| JP | 2004-513750 A | 5/2004 |
| JP | 2004-283523 | 10/2004 |
| JP | 2007-044203 | 2/2007 |
| JP | 2007-185348 | 7/2007 |
| JP | 2008-136556 A | 6/2008 |
| JP | 2008-279061 A | 11/2008 |
| JP | 2009-153664 A | 7/2009 |
| JP | 2010-526646 | 8/2010 |
| JP | 2014-068733 A | 4/2014 |
| KR | 20-0204510 Y1 | 11/2000 |
| WO | WO 00/24064 | 4/2000 |
| WO | WO 00/47108 A1 | 8/2000 |
| WO | WO 01/08552 A1 | 2/2001 |
| WO | WO 02/17782 A2 | 3/2002 |
| WO | WO 2005/010568 A2 | 2/2005 |
| WO | WO 2005/020121 A1 | 3/2005 |
| WO | WO 2005/110238 A1 | 11/2005 |
| WO | WO 2006/009830 A2 | 1/2006 |
| WO | WO 2006/067690 A2 | 6/2006 |
| WO | WO 2007/012931 A2 | 2/2007 |
| WO | WO 2007/053146 A1 | 5/2007 |
| WO | WO 2008/141306 A2 | 11/2008 |
| WO | WO 2013/019494 A2 | 2/2013 |
| WO | WO 2013/038296 A1 | 3/2013 |
| WO | WO 2013/109389 A1 | 7/2013 |
| WO | WO 2013/109390 A1 | 7/2013 |
| WO | WO 2014/092932 A1 | 6/2014 |

OTHER PUBLICATIONS

European Search Report, EP Application No. 13863449.8, Oct. 19, 2015, 3 pages.
European Search Report, EP Application No. 14743615.8, Oct. 12, 2015, 3 pages.
European Search Report, EP Application No. 14743839.4, Oct. 12, 2015, 3 pages.
Gibbs et al., "Reducing Motion Artifact in Wearable Bio-Sensors Using MEMS Accelerometers for Active Noise Cancellation," 2005 American Control Conference, Jun. 8-10, 2005, Portland, OR, USA, pp. 1581-1586.
International Preliminary Report on Patentability, PCT/US2014/012940, Jun. 17, 2015, 23 pages.
International Search Report and Written Opinion of the International Searching Authority, corresponding to International Patent Application No. PCT/US2014/012940, Date of Mailing: Oct. 16, 2014, 13 pages.
International Search Report corresponding to International Patent Application No. PCT/US2014/012909, Date of Mailing: May 13, 2014, 3 pages.
Notification Concerning Transmittal of International Preliminary Report on Patentability, PCT/US2014/012909, Jul. 28, 2015.
Notification of Transmittal of the International Search Report and the Written Opinion of the International Searching Authority, or the Declaration, PCT/US2015/014562, Oct. 28, 2015.
Notification of Transmittal of the International Search Report and the Written Opinion of the International Searching Authority, or the Declaration, PCT/US2015/042636, Oct. 29, 2015.
Notification of Transmittal of the International Search Report and the Written Opinion of the International Searching Authority, or the Declaration, PCT/US2015/042015, Oct. 29, 2015.
Notification of Transmittal of the International Search Report and the Written Opinion of the International Searching Authority, or the Declaration, PCT/US2015/042035, Oct. 29, 2015.
Wood et al., "Active Motion Artifact Reduction for Wearable Sensors Using Laguerre Expansion and Signal Separation," Proceedings of the 2005 IEEE Engineering in Medicine and Biology, $27^{th}$ Annual Conference, Shanghai, China, Sep. 1-4, 2005, pp. 3571-3574.
Notification of Transmittal of the International Search Report and the Written Opinion of the International Searching Authority, or the Declaration, PCT/US2015/046079, Dec. 29, 2015.
Communication pursuant to Article 94(3) EPC, European Patent Application No. 13863449.8, Nov. 5, 2015, 7 pages.
Communication pursuant to Article 94(3) EPC, European Patent Application No. 14743615.8, Dec. 23, 2015, 7 pages.
Communication pursuant to Article 94(3) EPC, European Patent Application No. 14743839.4, Dec. 23, 2015, 6 pages.
Communication pursuant to Article 94(3) EPC, European Patent Application No. 12820308.0, Feb. 3, 2016, 5 pages.
Notification of Transmittal of the International Search Report and Written Opinion of the International Search Authority issued May 26, 2016 by the Korean Intellectual Property Office for corresponding International Application No. PCT/US2016/019126.
Notification of Transmittal of the International Search Report and Written Opinion of the International Search Authority issued May 26, 2016 by the Korean Intellectual Property Office for corresponding International Application No. PCT/US2016/019132.
Asada, et al., "Mobile Monitoring with Wearable Photoplethysmographic Biosensors," IEEE Engineering in Medicine and Biology Magazine, May/Jun. 2003, pp. 28-40.
Bifulco et al., "Bluetooth Portable Device for Continuous ECG and Patient Motion Monitoring During Daily Life," Medicon 2007, IFMBE Proceedings 16, 2007, pp. 369-372.
Brodersen et al., "In-Ear Acquisition of Vital Signs Discloses New Chances for Preventive Continuous Cardiovascular Monitoring," 4th International Workshop on Wearable and Implantable Body Sensor Networks (BSN 2007), vol. 13 of the series IFMBE Proceedings, pp. 189-194.
Celka et al, "Motion Resistant Earphone Located Infrared based Heart Rate Measurement Device," Proceedings of the Second IASTED International Conference on Biomedical Engineering, Feb. 16-18, 2004, Innsbruck, Austria, pp. 582-585.
Communication Pursuant to Article 94(3) EPC, EP 12 739 502.8, Jul. 19, 2016, 7 pages.
Communication Pursuant to Article 94(3) EPC, EP 14 743 615.8, Jul. 19, 2016, 7 pages.
Communication Pursuant to Article 94(3) EPC, EP 14 743 839.4, Jul. 20, 2016, 5 pages.
Comtois et al., "A Wearable Wireless Reflectance Pulse Oximeter for Remote Triage Applications," 2006 IEEE, pp. 53-54.
Comtois, Gary, W., "Implementation of Accelerometer-Based Adaptive Noise Cancellation in a Wireless Wearable Pulse Oximeter Platform for Remote Physiological Monitoring and Triage," Thesis, Worcester Polytechnic Institute, Aug. 31, 2007, 149 pages.
Duun et al., "A Novel Ring Shaped Photodiode for Reflectance Pulse Oximetry in Wireless Applications," IEEE Sensors 2007 Conference, pp. 596-599.

(56) References Cited

OTHER PUBLICATIONS

Geun et al., "Measurement Site and Applied Pressure Consideration in Wrist Photoplethysmography," The 23rd International Technical Conference on Circuits/Systems, Computers and Communications, 2008, pp. 1129-1132.

Gibbs et al., "Active motion artifact cancellation for wearable health monitoring sensors using collocated MEMS accelerometers," Smart Structures and Materials, 2005: Sensors and Smart Structures Technologies for Civil, Mechanical, and Aerospace Systems, Proc. of SPIE, vol. 5765, pp. 811-819.

Haahr et al., "A Wearable "Electronic Patch" for Wireless Continuous Monitoring of Chronically Diseased Patients," Proceedings of the 5th International Workshop on Wearable and Implantable Body Sensor Networks, in conjunction with The 5th International Summer School and Symposium on Medical Devices and Biosensors, The Chinese University of Hong Kong, HKSAR, China, Jun. 1-3, 2008, pp. 66-70.

Jiang, Honghui, "Motion-Artifact Resistant Design of Photoplethysmograph Ring Sensor for Driver Monitoring," Thesis, Massachusetts Institute of Technology, Feb. 2004, 62 pages.

Kuzmina et al., "Compact multi-functional skin spectrometry set-up," Advanced Optical Materials, Technologies, and Devices, Proc. of SPIE, vol. 6596, 2007, pp. 65960T-1 to 65960T-6.

Lee et al, "Respiratory Rate Detection Algorithms by Photoplethysmography Signal Processing," 30th Annual International IEEE Embs Conference, Vancouver, British Columbia, Canada, Aug. 20-24, 2008, pp. 1140-1143.

Lindberg et al., "Monitoring of respiratory and heart rates using a fibre-optic sensor," Med Biol Eng Comput, Sep. 1992, vol. 30, No. 5, pp. 533-537.

Luprano, Jean, "Sensors and Parameter Extraction by Wearable Systems: Present Situation and Future," pHealth 2008, May 21, 2008, 29 pages.

Lygouras et al., "Optical-Fiber Finger Photo-Plethysmograph Using Digital Techniques," IEEE Sensors Journal, vol. 2, No. 1, Feb. 2002, pp. 20-25.

Maguire et al., "The Design and Clinical Use of a Reflective Brachial Photoplethysmograph," Technical Report NUIM/SS/—/2002/04, Submitted Apr. 2002, Signals and Systems Research Group, National University of Ireland, Maynooth, Co. Kildare, Ireland, 13 pages.

Mendelson et al., "Measurement Site and Photodetector Size Considerations in Optimizing Power Consumption of a Wearable Reflectance Pulse Oximeter," Proceedings of the 25th Annual International Conference of the IEEE EMBS, Cancun, Mexico, Sep. 17-21, 2003, pp. 3016-3019.

Mendelson et al., "Noninvasive Pulse Oximetry Utilizing Skin Reflectance Photoplethysmography," IEEE Transactions on Biomedical Engineering, vol. 35, No. 10, Oct. 1988, pp. 798-805.

Poh et al., "Motion Tolerant Magnetic Earring Sensor and Wireless Earpiece for Wearable Photoplethysmography," IEEE Transactions on Information Technology in Biomedicine, vol. 14, No. 3, May 2010, pp. 786-794.

Renevey et al., "Wrist-Located Pulse Detection Using IR Signals, Activity and Nonlinear Artifact Cancellation," IEEE EMBS, 2001, 4 pages.

Rhee et al., "Artifact-Resistant Power-Efficient Design of Finger-Ring Plethysmographic Sensors," IEEE Transactions on Biomedical Engineering, vol. 48, No. 7, Jul. 2001, pp. 795-805.

Shaltis, Phillip Andrew, Analysis and Validation of an Artifact Resistant Design for Oxygen Saturation Measurement Using Photo Plethysmographic Ring Sensors, Thesis, Massachusetts Institute of Technology, Jun. 2004, 103 pages.

Shin et al., "A Novel Headset with a Transmissive PPG Sensor for Heart Rate Measurement," ICBME 2008, Proceedings 23, 2009, pp. 519-522.

Spigulis et al, "Wearable wireless photoplethysmography sensors," Proc. of SPIE, vol. 6991, 2008, pp. 699120-1 to 699120-7.

Takatani et al., "Optical Oximetry Sensors for Whole Blood and Tissue," IEEE Engineering in Medicine and Biology, Jun./Jul. 1994, pp. 347-357.

Vogel et al., "A System for Assessing Motion Artifacts in the Signal of a Micro-Optic In-Ear Vital Signs Sensor," 30th Annual International IEEE EMBS Conference, Vancouver, British Columbia, Canada, Aug. 20-24, 2008.

Vogel et al., "In-Ear Heart Rate Monitoring Using a Micro-Optic Reflective Sensor," Proceedings of the 29th Annual International Conference of the IEEE EMBS Cite Internationale, Lyon, France, Aug. 23-26, 2007, pp. 1375-1378.

Wang et al., "Multichannel Reflective PPG Earpiece Sensor With Passive Motion Cancellation," IEEE Transactions on Biomedical Circuits and Systems, vol. 1, No. 4, Dec. 2007, pp. 235-241.

Wang et al., "Reflective Photoplethysmograph Earpiece Sensor for Ubiquitous Heart Rate Monitoring," 4th International Workshop on Wearable and Implantable Body Sensor Networks, 2007, vol. 13 of the series IFMBE Proceedings, pp. 179-183.

Wei et al. "A New Wristband Wearable Sensor Using Adaptive Reduction Filter to Reduce Motion Artifact," Proceedings of the 5th International Conference on Information Technology and Application in Biomedicine, in conjunction with The 2nd International Symposium & Summer School on Biomedical and Health Engineering, Shenzhen, China, May 30-31, 2008, pp. 278-281.

Wood, Levi Benjamin, "Motion Artifact Reduction for Wearable Photoplethysmogram Sensors Using Micro Accelerometers and Laguerre Series Adaptive Filters," Thesis, Massachusetts Institute of Technology, Jun. 2008, 74 pages.

Han et al., "Artifacts in wearable photoplethysmographs during daily life motions and their reduction with least mean square based active noise cancellation method," Computers in Biology and Medicine, 42, 2012, pp. 387-393.

Extended European Search Report, EP Application No. 16164775.5 Sep. 13, 2016, 7 pages.

Notification of Transmittal of the International Search Report and the Written Opinion of the International Searching Authority, or the Declaration, PCT/US2016/041842, Oct. 21, 2016, 5 pages.

Notification of Transmittal of International Preliminary Report on Patentability, PCT/US2015/041562, Oct. 20, 2016, 14 pages.

Notification of Transmittal of International Preliminary Report on Patentability, PCT/US2015/042636, Oct. 20, 2016, 7 pages.

Notification of Transmittal of International Preliminary Report on Patentability, PCT/US2015/042015, Oct. 20, 2016, 10 pages.

Notification of Transmittal of International Preliminary Report on Patentability, PCT/US2015/042035, Oct. 20, 2016, 8 pages.

Notification of Transmittal of International Preliminary Report on Patentability, PCT/US2015/046079, Oct. 20, 2016, 10 pages.

"U.S. Army Fitness Training Handbook" by the Department of the Army, 2003, The Lyons Press. p. 17.

"Warfighter Physiological and Environmental Monitoring: A Study for the U.S. Army Research Institute in Environmental Medicine and the Soldier Systems Center", Massachusetts Institute of Technology Lincoln Laboratory, Final Report, Nov. 1, 2004, prepared for the U.S. Army under Air Force Contract F19628-00-C-0002; approved for public release.

Anpo et al. "Photocatalytic Reduction of $CO_2$ With $H_2O$ on Titanium Oxides Anchored within Micropores of Zeolites: Effects of the Structure of the Active Sites and the Addition of Pt" *J. Phys. Chem. B*, 101:2632-2636 (1997).

Bârsan et al. "Understanding the fundamental principles of metal oxide based gas sensors; the example of CO sensing with $SnO_2$ sensors in the presence of humidity" *Journal of Physics: Condensed Matter* 15:R813-R839 (2003).

Bott "Electrochemistry of Semiconductors" *Current Separations* 17(3):87-91 (1998).

Colligan, M. J. et al. in "The psychological effects of indoor air pollution", Bulletin of the New York Academy of Medicine, vol. 57, No. 10, Dec. 1981, p. 1014-1026.

de Paula Santos, U. et al, in "Effects of air pollution on blood pressure and heart rate variability: a panel study of vehicular traffic controllers in the city of Sao Paulo, Brazil", European Heart Journal (2005) 26, 193-200.

(56) References Cited

OTHER PUBLICATIONS

Ebert, T et al., "Influence of Hydration Status on Thermoregulation and Cycling Hill Climbing," Med. Sci. Sport Exerc. vol. 39, No. 2, pp. 323-329, 2007.
European Search Report corresponding to European Application No. 07862660.3 dated Apr. 25, 2012; 7 pages.
Falkner et al, "Cardiovascular response to mental stress in normal adolescents with hypertensive parents. Hemodynamics and mental stress in adolescents," *Hypertension* 1979, 1:23-30.
FiTrainer "The Only Trainer You Need"; http://itami.com; Downloaded Feb. 26, 2010; © 2008 FiTriainer™; 2 pages.
Fleming et al., "A Comparison of Signal Processing Techniques for the Extraction of Breathing Rate from the Photopethysmorgram," World Academy of Science, Engineering and Technology, vol. 30, Oct. 2007, pp. 276-280.
Geladas et al., "Effect of cold air inhalation on core temperature in exercising subjects under stress," The American Physiological Society, pp. 2381-2387, 1988.
Gibbs et al., "Reducing Motion Artifact Reduction for Wearable Sensors Using MEMS Accelerometers for Active Noise Cancellation," 2005 American Control Conference, Jun. 8-10, 2005, Portland, OR, USA, pp. 1581-1586.
Gold, D.R. et al. in "Ambient Pollution and Heart Rate Variability", Circulation 2000, 101:1267-1273.
International Search Report corresponding to International Patent Application No. PCT/US2012/046446, Date of Mailing: Jan. 14, 2013, 3 pages.
International Search Report and Written Opinion of the International Searching Authority, corresponding to PCT/US2012/0948079, mailed Oct. 9, 2012.
International Search Report and Written Opinion of the International Searching Authority, corresponding to PCT/US2007/025114, mailed May 13, 2008.
International Search Report Corresponding to International Application No. PCT/US2012/022634, Date of Mailing: Aug. 22, 2012, 9 pages.
Maomao et al., "Mobile Context-Aware Game for the Next Generation," $2^{nd}$ International Conference on Application and Development of Computer Games ADCOG 2003, p. 78-81.
Martins et al. "Zinc oxide as an ozone sensor" *Journal of Applied Physics* 96(3):1398-1408 (2004).
Maughan, R.J., "Impact of mild dehydration on wellness and on exercise performance," European Journal of Clinical Nutrition, 57, Suppl. 2, pp. S19-S23, 2003.
Maughan et al., "Exercise, Heat, Hydration and the Brain," Journal of the American College of Nutrition, vol. 26, No. 5, pp. 604S-612S, 2007.
Mostardi, R., et al., "The effect of increased body temperature due to exercise on the heart rate and the maximal aerobic power," Europ. J. Appl. Physiol, 33, pp. 237-245, 1974.
Nakajima et al., "Monitoring of heart and respiratory rates by photoplethyusmography using a digital filtering technique," Med. Eng. Phys., vol. 18, No. 5, Jul. 1996, pp. 365-372.
Notification of Transmittal of the International Search Report and Written Opinion of the International Search Authority issued Jul. 30, 2010 by the Korean Intellectual Property Office for corresponding International Application No. PCT/US2010/021936.
Notification of Transmittal of the International Search Report and Written Opinion of the International Search Authority issued Aug. 26, 2010 by the Korean Intellectual Property Office for corresponding International Application No. PCT/US2010/021629.
Notification of Transmittal of the International Search Report and the Written Opinion of the International Search Authority issued Sep. 16, 2010 by the Korean Intellectual Property Office for corresponding International Application No. PCT/US2010/024922.
Notification of Transmittal of the International Search Report and the Written Opinion of the International Search Authority issued Sep. 27, 2010 by the Korean Intellectual Property Office for corresponding International Application No. PCT/US2010/025216.
Notification of Transmittal of the International Search Report and the Written Opinion of the International Searching Authority, or the Declaration corresponding to International Application No. PCT/US2013/070271; Date of Mailing: Feb. 26, 2014; 13 pages.
Saladin et al. "Photosynthesis of $CH_4$ at a $TiO_2$ Surface from Gaseous $H_2O$ and $CO_2$" *J. Chem. Soc., Chem. Commun.* 533-534 (1995).
Shorten et al., "Acute effect of environmental temperature during exercise on subsequent energy intake in active men," Am. J Clin. Nutr. 90, pp. 1215-1221, 2009.
Skubal et al. "Detection and identification of gaseous organics using a $TiO_2$ sensor" *Journal of Photochemistry and Photobiology A: Chemistry* 148:103-108 (2002).
Skubal et al. "Monitoring the Electrical Response of Photoinduced Organic Oxideation on $TiO_2$ Surfaces" Manuscript submitted Oct. 2000 to SPIE Intl. Symposium on Environment & Industrial Sensing, Boston, MA, Nov. 5-8, 2000, sponsored by SPIE, 10 pp.
Thompson, M.W., "Cardiovascular drift and critical core temperature: factors limiting endurance performance in the heat?" J. Exerc. Sci. Fit, vol. 4, No. 1, pp. 15-24, 2006.
Wood et al., "Active Motion Artifact Reduction for Wearable Sensors Using Laguerre Expansion and Signal Separator," Proceedings of the 2005 IEEE Engineering in Medicine and Biology, $27^{th}$ Annual Conference, Shanghai, China, Sep. 1-4, 2005, pp. 3571-3574.
Zhang et al. "Development of Chemical Oxygen Demand On-Line Monitoring System Based on a Photoelectrochemical Degradation Principle" *Environ. Sci. Technol.*, 40(7):2363-2368 (2006).
Communication and Supplementary European Search Report, EP Application No. 15844956.1, Aug. 16, 2017, 7 pp.

\* cited by examiner

EARBUD INSIDE EAR
CORRECT ANGLE

EARBUD INSIDE EAR
WRONG ANGLE

METHODS AND APPARATUS FOR IMPROVING SIGNAL QUALITY IN WEARABLE BIOMETRIC MONITORING DEVICES

RELATED APPLICATIONS

This application claims the benefit of and priority to U.S. Provisional Patent Application No. 62/056,510 filed Sep. 27, 2014, and U.S. Provisional Patent Application No. 62/110,655 filed Feb. 2, 2015, the disclosures of which are incorporated herein by reference as if set forth in their entireties.

FIELD OF THE INVENTION

The present invention relates generally to monitoring devices and methods, more particularly, to monitoring devices and methods for measuring physiological information.

BACKGROUND OF THE INVENTION

Photoplethysmography (PPG) is based upon shining light into the human body and measuring how the scattered light intensity changes with each pulse of blood flow. The scattered light intensity will change in time with respect to changes in blood flow or blood opacity associated with heart beats, breaths, blood oxygen level ($SpO_2$), and the like. Such a sensing methodology may require the magnitude of light energy reaching the volume of flesh being interrogated to be steady and consistent so that small changes in the quantity of scattered photons can be attributed to varying blood flow. If the incidental and scattered photon count magnitude changes due to light coupling variation between the source or detector and the skin or other body tissue, then the signal of interest can be difficult to ascertain due to large photon count variability caused by motion artifacts. Changes in the surface area (and volume) of skin or other body tissue being impacted with photons, or varying skin surface curvature reflecting significant portions of the photons may also significantly impact optical coupling efficiency. Physical activity, such as walking, cycling, running, etc., may cause motion artifacts in the optical scatter signal from the body, and time-varying changes in photon intensity due to motion artifacts may swamp-out time-varying changes in photon intensity due to blood flow changes. Environmental artifacts, such as ambient light noise, as well as motion-coupled ambient light noise can further swamp-out blood-flow related signals. Each of these changes in optical coupling can dramatically reduce the signal-to-noise ratio (S/N) of biometric PPG information to total time-varying photonic interrogation count. This can result in a much lower accuracy in metrics derived from PPG data, such as heart rate and breathing rate.

The signal quality from a biometric sensor, such as a PPG sensor, in a wearable monitoring device increases when the monitoring device is worn correctly and decreases when the monitoring device is worn incorrectly. For example, a user may go for a run with a biometric earbud and expect accurate heart rate zone information from the sensor(s) therein, only to find the sensor data is erroneous due to a poor fitting of the biometric earbud within the ear. Unfortunately, without some way to measure signal quality, a user may not know if sensor signal quality is adequate.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

According to some embodiments of the present invention, a wearable biometric monitoring device is configured to assess the biometric signal quality of one or more sensors associated with the biometric monitoring device, determine how the user should adjust the device to improve the biometric fit, and instruct the user to wear the device a certain way (e.g., audio-visually via a remote device). In some embodiments, this may involve an iterative approach. In some embodiments, communicating instructions to a user may include instructing the user to execute a testing regimen while wearing the device. The testing regimen facilitates an estimation of signal quality that can be used to provide feedback to the user that he/she needs to adjust the device to improve the biometric fit (and hence the biometric signal quality).

According to some embodiments of the present invention, a method of monitoring signal quality of a wearable biometric monitoring device having at least one sensor configured to detect and/or measure physiological information from a subject wearing the biometric monitoring device and at least one processor in communication with the at least one sensor that is configured to receive and analyze signals produced by the at least one sensor includes instructing the subject via the at least one processor to begin an exercise regimen, measuring signal quality produced by the at least one sensor during the exercise regimen, and communicating information to the subject regarding the signal quality during the exercise regimen. In some embodiments, the biometric monitoring device is configured to be integrated within an earbud. In some embodiments, the biometric monitoring device is configured to be integrated within an audio headset, a wrist strap, a wrist watch, an ankle bracelet, an armband, etc. In other embodiments, the biometric monitoring device comprises a band that configured to at least partially encircle a portion of the body of a subject, such as a limb, a nose, an earlobe, and/or a digit, etc.

In some embodiments, instructing the subject to begin an exercise regimen comprises sending an audio and/or visual communication to a remote device (e.g., a smartphone, computer, etc.) in communication with the biometric monitoring device. In other embodiments, instructing the subject to begin an exercise regimen comprises causing the biometric monitoring device and/or a remote device to vibrate.

Communicating information to the subject regarding the signal quality may include communicating instructions to the subject to adjust the biometric monitoring device relative to the body of the subject if the signal quality is below a threshold level. Communicating information to the subject regarding the signal quality also may include communicating information to the subject that the signal quality is above a threshold level.

In some embodiments, communicating information to the subject regarding the signal quality comprises sending an audio and/or visual communication to a remote device in communication with the biometric monitoring device. In other embodiments, communicating information to the subject regarding the signal quality comprises causing the biometric monitoring device and/or a remote device to vibrate.

In some embodiments, the biometric monitoring device includes an actuator, and the method further comprises automatically adjusting the biometric monitoring device relative to the body of the subject via the actuator if the signal quality is below a threshold level.

In some embodiments, the biometric monitoring device includes a motion sensor, and the method further comprises determining if the subject has begun the exercise regimen by detecting a change in subject activity via the motion sensor.

In some embodiments, the biometric monitoring device includes a motion sensor, and the method further comprises determining if the subject is wearing the biometric monitoring device by determining if body motion over a period of time is above a threshold.

According to some embodiments of the present invention, a method of generating a physiological assessment of a subject includes collecting physiological information and/or motion information from the subject via at least one wearable device having at least one physiological sensor and/or at least one motion sensor, determining a quality level for the physiological information and/or motion information at one or more selected times during the period of time, and generating a physiological assessment for the subject using the physiological information and/or motion information at the one or more selected times that has a quality level above a threshold level.

According to some embodiments of the present invention, a method of generating a physiological assessment of a subject includes collecting physiological information and/or motion information from a subject via at least one wearable device having at least one physiological sensor and/or at least one motion sensor, determining one or more time periods when the wearable device is being worn by the subject, and generating a physiological assessment for the subject using the physiological information and/or motion information obtained during the one or more time periods when the wearable device is being worn by the subject.

According to some embodiments of the present invention, a method of detecting if a biometric monitoring device having a PPG sensor is being worn by a subject includes processing data produced by the PPG sensor via at least one processor to determine one or more of the following: whether intensity of a DC component of a PPG signal from the PPG sensor is within a predetermined range, whether at least one vital sign of the subject is detected, and whether a heart rate value of the subject is within a predetermined range. In some embodiments, the processor may generate an indication as to whether or not the biometric monitoring device is being worn by the subject. In some embodiments, the biometric monitoring device is integrated within an earbud, an audio headset, a wrist strap, a wrist watch, an ankle bracelet, or an armband. In some embodiments, the biometric monitoring device comprises a band configured to at least partially encircle a portion of the body of a subject, and wherein the portion of the body comprises a limb, a nose, an earlobe, and/or a digit.

According to some embodiments of the present invention, a method of detecting if a biometric monitoring device having a PPG sensor and at least one processor is being worn by a subject includes determining quality of a signal produced by the PPG sensor, making an estimate as to whether the biometric monitoring device is being worn based on the signal produced by the PPG sensor, and determining whether the biometric monitoring device is being worn by processing the signal in context with the quality of the signal. In some embodiments, the at least one processor may generate an indication as to whether or not the biometric monitoring device is being worn by the subject. In some embodiments, the biometric monitoring device is integrated within an earbud, an audio headset, a wrist strap, a wrist watch, an ankle bracelet, or an armband. In some embodiments, the biometric monitoring device comprises a band configured to at least partially encircle a portion of the body of a subject, and wherein the portion of the body comprises a limb, a nose, an earlobe, and/or a digit.

According to some embodiments of the present invention, a method of detecting if a biometric monitoring device having a motion sensor and at least one processor is being worn by a subject includes determining quality of a signal produced by the motion sensor, making an estimate as to whether the biometric monitoring device is being worn based on the signal produced by the motion sensor, and determining whether the biometric monitoring device is being worn by processing the signal in context with the quality of the signal. In some embodiments, the at least one processor may generate an indication as to whether or not the biometric monitoring device is being worn by the subject. In some embodiments, the biometric monitoring device is integrated within an earbud, an audio headset, a wrist strap, a wrist watch, an ankle bracelet, or an armband. In some embodiments, the biometric monitoring device comprises a band configured to at least partially encircle a portion of the body of a subject, and wherein the portion of the body comprises a limb, a nose, an earlobe, and/or a digit.

According to some embodiments of the present invention, a method of monitoring signal quality of a wearable biometric monitoring device is provided. The biometric monitoring device includes at least one physiological sensor (e.g., a PPG sensor, etc.) configured to detect physiological and at least one sensor (e.g., an accelerometer, etc.) configured to detect motion information from a subject wearing the biometric monitoring device and at least one processor in communication with the at least one sensor that is configured to receive and analyze signals produced by the at least one sensor. The method includes measuring quality of a signal produced by the physiological sensor during an exercise regimen that includes factoring an amount of physiological information in the signal in comparison with an amount of motion information in the signal. Factoring the amount of physiological information in the signal in comparison with the amount of motion information in the signal includes calculating a ratio of physiological information and motion information.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

The accompanying drawings, which form a part of the specification, illustrate various embodiments of the present invention. The drawings and description together serve to fully explain embodiments of the present invention.

DETAILED DESCRIPTION

Figure 1:
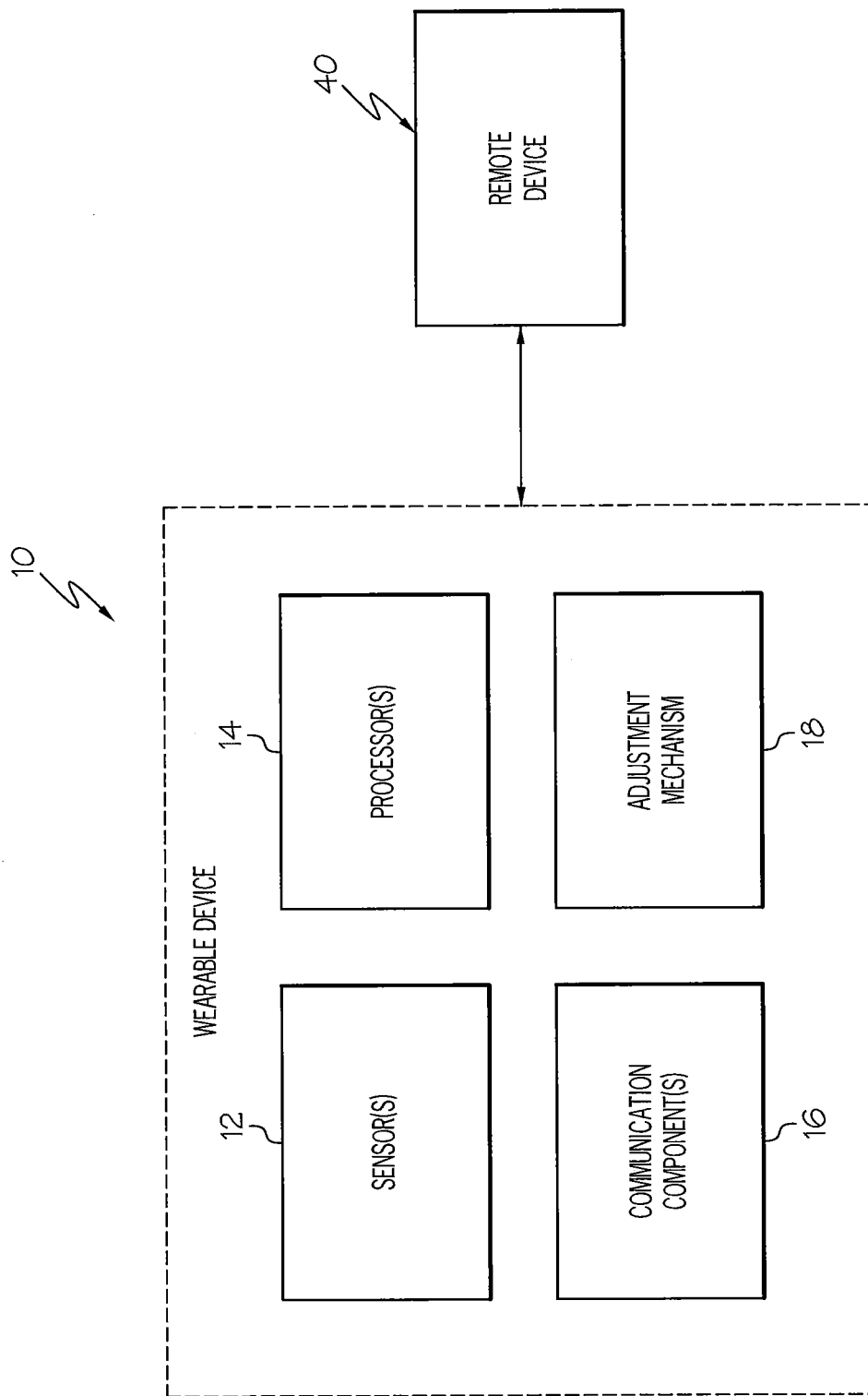
FIG. 1 is a block diagram of a wearable biometric monitoring device that can communicate with a remote device, such as a smartphone, and that can assess the biometric signal quality of one or more sensors associated with the device, according to some embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. Features described with respect to one figure or embodiment can be associated with another embodiment or figure although not specifically described or shown as such.

It will be understood that when a feature or element is referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "secured", "connected", "attached" or "coupled" to another feature or element, it can be directly secured, directly connected, attached or coupled to the other feature or element or intervening features or elements may be present. In contrast, when a feature or element is referred to as being "directly secured", "directly connected", "directly attached" or "directly coupled" to another feature or element, there are no intervening features or elements present. Although described or shown with respect to one embodiment, the features and elements so described or shown can apply to other embodiments.

The terminology used herein is for the purpose of describing particular embodiments only and is not intended to be limiting of the invention. As used herein, the singular forms "a", "an" and "the" are intended to include the plural forms as well, unless the context clearly indicates otherwise.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

As used herein, the term "and/or" includes any and all combinations of one or more of the associated listed items and may be abbreviated as "/".

As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that although the terms first and second are used herein to describe various features or elements, these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "about", as used herein with respect to a value or number, means that the value or number can vary more or less, for example by +/−20%, +/−10%, +/−5%, +/−1%, +/−0.5%, +/−0.1%, etc.

The terms "sensor", "sensing element", and "sensor module", as used herein, are interchangeable and refer to a sensor element or group of sensor elements that may be utilized to sense information, such as information (e.g., physiological information, body motion, etc.) from the body of a subject and/or environmental information in a vicinity of the subject. A sensor/sensing element/sensor module may comprise one or more of the following: a detector element, an emitter element, a processing element, optics, mechanical support, supporting circuitry, and the like. Both a single sensor element and a collection of sensor elements may be considered a sensor, a sensing element, or a sensor module.

The term "optical emitter", as used herein, may include a single optical emitter and/or a plurality of separate optical emitters that are associated with each other.

The term "optical detector", as used herein, may include a single optical detector and/or a plurality of separate optical detectors that are associated with each other.

The term "wearable sensor module", as used herein, refers to a sensor module configured to be worn on or near the body of a subject.

The terms "monitoring device", "biometric monitoring device" and "biometric monitor", as used herein, are interchangeable and include any type of device, article, or clothing that may be worn by and/or attached to a subject and that includes at least one sensor/sensing element/sensor module. Exemplary monitoring devices may be embodied in an earpiece, a headpiece, a finger clip, a digit (finger or toe) piece, a limb band (such as an arm band or leg band), an ankle band, a wrist band, a nose piece, a sensor patch, eyewear (such as glasses or shades), apparel (such as a shirt, hat, underwear, etc.), a mouthpiece or tooth piece, contact lenses, or the like.

The term "monitoring" refers to the act of measuring, quantifying, qualifying, estimating, sensing, calculating, interpolating, extrapolating, inferring, deducing, or any combination of these actions. More generally, "monitoring" refers to a way of getting information via one or more sensing elements. For example, "blood health monitoring" includes monitoring blood gas levels, blood hydration, and metabolite/electrolyte levels.

The term "headset", as used herein, is intended to include any type of device or earpiece that may be attached to or near the ear (or ears) of a user and may have various configurations, without limitation. Headsets incorporating biometric monitoring devices, as described herein, may include mono headsets (a device having only one earbud, one earpiece, etc.) and stereo headsets (a device having two earbuds, two earpieces, etc.), earbuds, hearing aids, ear jewelry, face masks, headbands, and the like. In some embodiments, the term "headset" may include broadly headset elements that are not located on the head but are associated with the headset. For example, in a "medallion" style wireless headset, where the medallion comprises the wireless electronics and the headphones are plugged into or hard-wired into the medallion, the wearable medallion would be considered part of the headset as a whole. Similarly, in some cases, if a mobile phone or other mobile device is intimately associated with a plugged-in headphone, then the term "headset" may refer to the headphone-mobile device combination. The terms "headset" and "earphone", as used herein, are interchangeable.

The term "physiological" refers to matter or energy of or from the body of a creature (e.g., humans, animals, etc.). In embodiments of the present invention, the term "physiological" is intended to be used broadly, covering both physical and psychological matter and energy of or from the body of a creature.

The term "body" refers to the body of a subject (human or animal) that may wear a monitoring device, according to embodiments of the present invention.

The term "processor" is used broadly to refer to a signal processor or computing system or processing or computing method which may be localized or distributed. For example, a localized signal processor may comprise one or more signal processors or processing methods localized to a general location, such as to a wearable device. Examples of such wearable devices may comprise an earpiece, a headpiece, a finger clip, a digit (finger or toe) piece, a limb band (such as an arm band or leg band), an ankle band, a wrist band, a nose piece, a sensor patch, eyewear (such as glasses or shades), apparel (such as a shirt, hat underwear, etc.), a mouthpiece or tooth piece, contact lenses, or the like. Examples of a distributed processor comprise "the cloud", the internet, a remote database, a remote processor computer, a plurality of remote processors or computers in communication with each other, or the like, or processing methods distributed amongst one or more of these elements. The key difference is that a distributed processor may include delocalized elements, whereas a localized processor may work independently of a distributed processing system. As a specific example, microprocessors, microcontrollers, ASICs (application specific integrated circuit), analog processing circuitry, or digital signal processors are a few non-limiting examples of physical signal processors that may be found in wearable devices.

The term "remote" does not necessarily mean that the "remote device" is a wireless device or that it is a long distance away from a device in communication with a "remote device". Rather, the term "remote" is used to reference a device or system that is distinct from another device or system or that is not substantially reliant on another device or system for core functionality. For example, a computer wired to wearable device may be considered a remote device, as the two devices are distinct and/or not substantially reliant on each other for core functionally. However, any wireless device (such as a portable device, for example) or system (such as a remote database for example) is considered remote to any other wireless device or system.

The term "RRi" refers to "R-R interval" in the electrocardiogram or photoplethysmogram of a person. Generally, where heart rate is used in embodiments of the present invention, RRi may also be applied in a similar manner. However, RRi and heart rate are generally related in an inverse fashion, such that 1/RRi=instantaneous heart rate.

The term "HRV" refers to "heart rate variability" or "R-R variability", which is a statistical representation of a group of consecutive R-R intervals or N-N intervals (beat-to-beat intervals between consecutive heart beats). The types of statistics performed to generate an HRV value can be quite numerous and broad. In general, a variety of different time-domain and/or frequency domain statistics on heart beat intervals can be described as different HRV values. As one specific example of HRV, 2- or 5-minutes worth of R-R intervals may be processed to determine the mean and standard deviation (SDNN), which is a representation of HRV. In general, the higher the SDNN for a group of R-R intervals collected from a person, the more relaxed, physically fit, or healthy that person may be. N-N intervals may be collected via photoplethysmograms (PPG), electrocardiograms (ECG), blood pressure pulses, ballistocardiograms (BCG), and the like.

In the following figures, various monitoring devices will be illustrated and described for attachment to the ear or an appendage of the human body. However, it is to be understood that embodiments of the present invention are not limited to the illustrated monitoring devices or to those worn by humans.

The ear is an ideal location for wearable health and environmental monitors. The ear is a relatively immobile platform that does not obstruct a person's movement or vision. Monitoring devices located at an ear have, for example, access to the inner-ear canal and tympanic membrane (for measuring core body temperature), muscle tissue (for monitoring muscle tension), the pinna, earlobe, and elsewhere (for monitoring blood gas levels), the region behind the ear (for measuring skin temperature and galvanic skin response), and the internal carotid artery (for measuring cardiopulmonary functioning), etc. A particularly distinct pulsatile blood flow waveform can be discerned optically, via PPG, between the anti-tragus and concha region of the ear. The ear is also at or near the point of exposure to: environmental breathable toxicants of interest (volatile organic compounds, pollution, etc.); noise pollution experienced by the ear; and lighting conditions for the eye. Furthermore, as the ear canal is naturally designed for transmitting acoustical energy, the ear provides a good location for monitoring internal sounds, such as heartbeat, breathing rate, and mouth motion.

FIG. 1 is a schematic diagram of a wearable monitoring device 10, according to some embodiments of the present invention. The wearable biometric monitoring device 10 may be an earbud module configured to be positioned within the ear of a subject, may be in the form of a sensor band configured to be secured to an appendage (e.g., an arm, wrist, hand, finger, toe, leg, foot, neck, etc.) of a subject, may be worn internally in the body (e.g., within the mouth as with a mouth guard, etc.), may be a sensor device configured to be adhesively secured to any portion of the body of a subject. Wearable monitoring devices, according to some embodiments of the present invention, may also be integrated within an audio headset, a wrist strap, a wrist watch, an ankle bracelet, a headband, an armband, etc. Wearable monitoring devices, according to some embodiments of the present invention, may also be utilized in various devices and articles including, but not limited to, patches, clothing, etc. Embodiments of the present invention can be utilized wherever PPG and blood flow signals can be obtained and at any location on the body of a subject. Embodiments of the present invention are not limited to the illustrated monitoring devices.

Figure 2B:
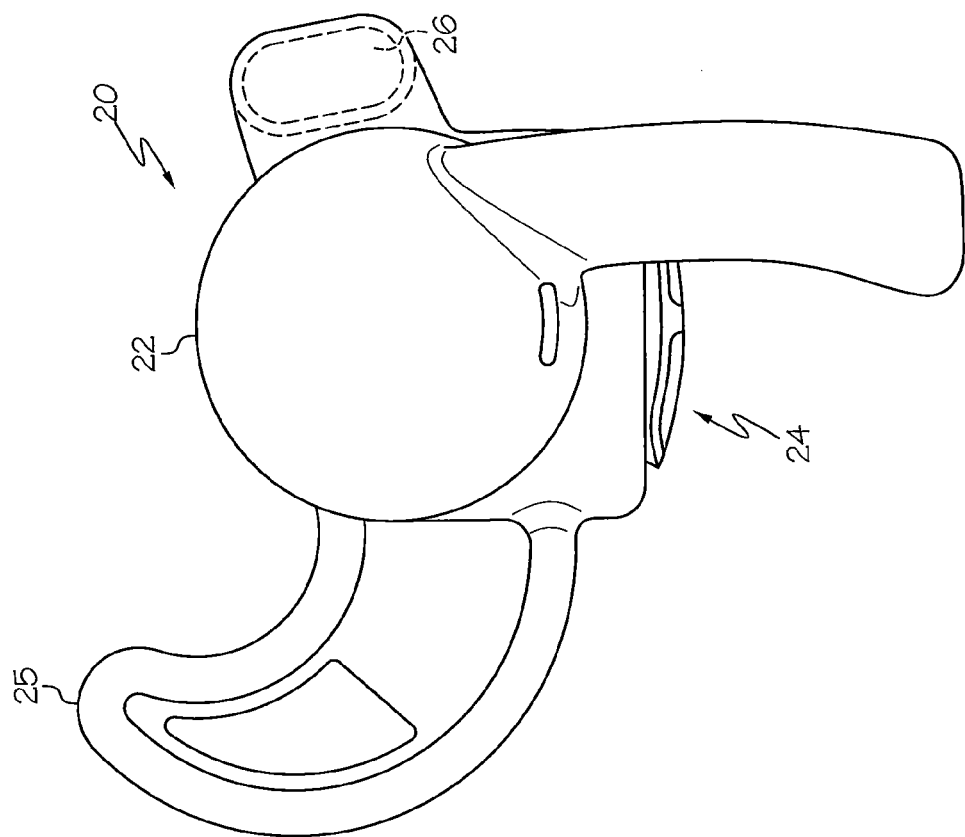
FIGS. 2A-2B illustrate a biometric monitoring device that can be positioned within an ear of a subject, according to some embodiments of the present invention.
Figure 2A:
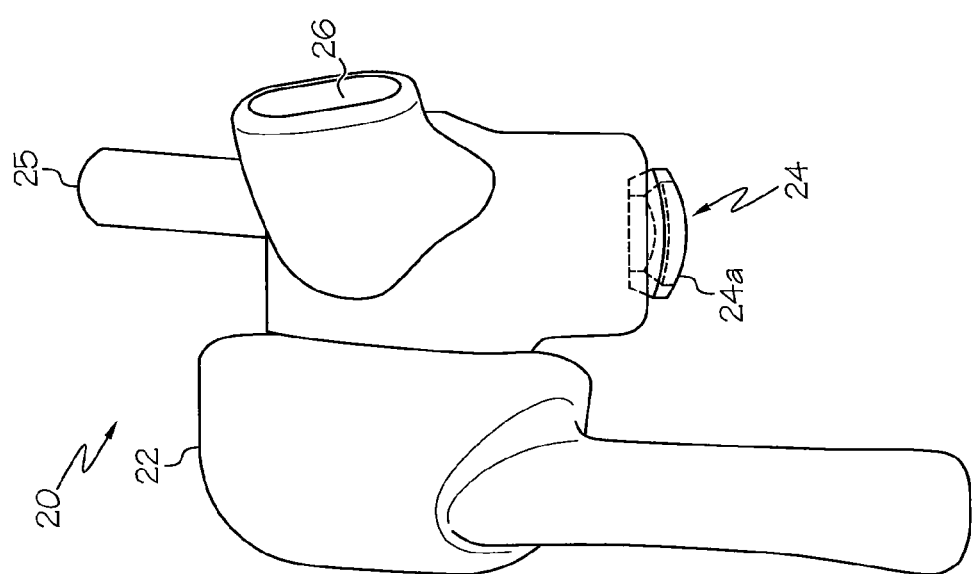

FIGS. 2A-2B illustrate a monitoring apparatus 20 configured to be secured to an ear of a subject and that may function as the monitoring device 10 of FIG. 1, according to some embodiments of the present invention. The illustrated apparatus 20 includes an earpiece body or housing 22, a sensor module 24, a stabilizer 25, and a sound port 26. When positioned within the ear of a subject, the sensor module 24 has a region 24a configured to contact a selected area of the ear. The illustrated sensor region 24a may be contoured (i.e., is "form-fitted") to matingly engage a portion of the ear between the anti tragus and acoustic meatus, and the stabilizer is configured to engage the anti-helix. However, monitoring devices in accordance with embodiments of the present invention can have sensor modules with one or more regions configured to engage various portions of the ear. Various types of device configured to be worn at or near the ear may be utilized in conjunction with embodiments of the present invention.

Figure 3A:
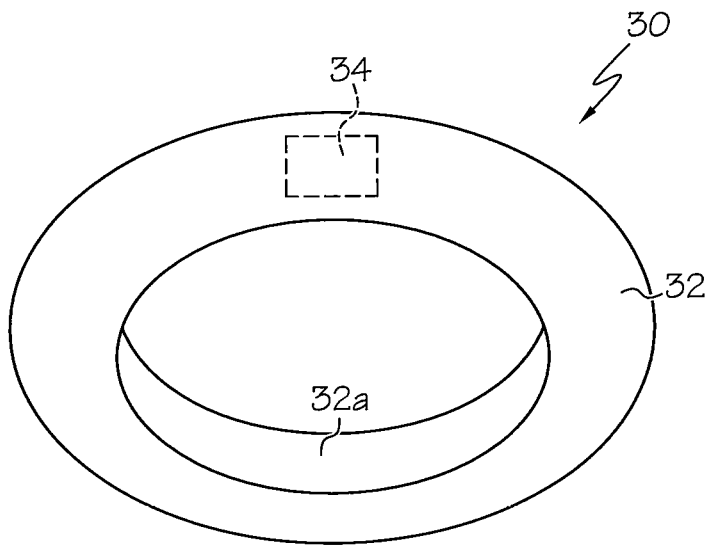
FIG. 3A illustrates a biometric monitoring device that can be positioned around an appendage of the body of a subject, according to some embodiments of the present invention.
Figure 3B:
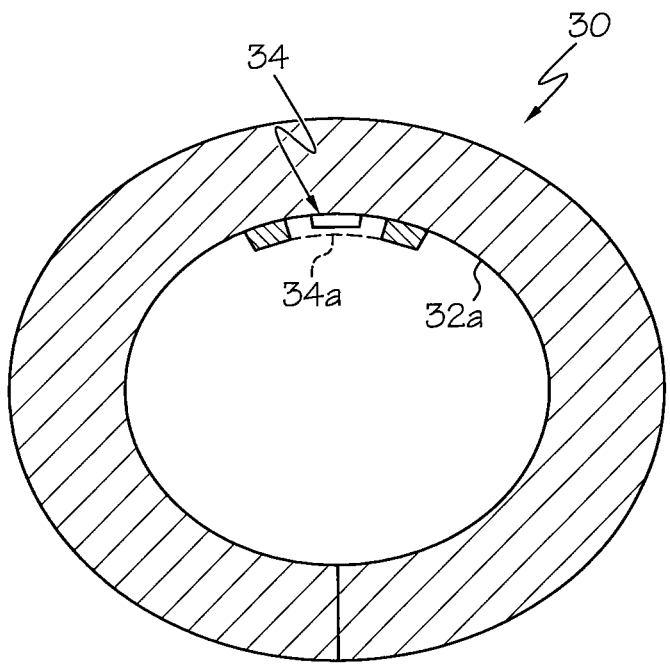
FIG. 3B is a cross sectional view of the biometric monitoring device of FIG. 3A.

FIGS. 3A-3B illustrate a monitoring apparatus 30 in the form of a sensor strap or band 32 configured to be secured to an appendage (e.g., an arm, wrist, hand, finger, toe, leg, foot, neck, etc.) of a subject and that may function as the monitoring device 10 of FIG. 1, according to some embodiments of the present invention. The band 32 includes a sensor module 34 on or extending from the inside surface 32a of the band 32. The sensor module 34 is configured to detect and/or measure physiological information from the subject and includes a sensor region 34a that may be contoured to contact the skin of a subject wearing the apparatus 30.

Embodiments of the present invention may be utilized in various devices and articles including, but not limited to, patches, clothing, etc. Embodiments of the present invention can be utilized wherever PPG and blood flow signals can be obtained and at any location on the body of a subject. Embodiments of the present invention are not limited to the illustrated monitoring devices.

The sensor modules 24, 34 for the illustrated monitoring devices 20, 30 of FIGS. 2A-2B and 3A-3B are configured to detect and/or measure physiological information from the subject. In some embodiments, the sensor modules 24, 34 may be configured to detect and/or measure one or more environmental conditions in a vicinity of the subject wearing the monitoring device 20, 30.

A sensor module utilized in accordance with embodiments of the present invention may be an optical sensor module that includes at least one optical emitter and at least one optical detector. Exemplary optical emitters include, but are not limited to light-emitting diodes (LEDs), laser diodes (LDs), organic light-emitting diodes (OLEDs), compact incandescent bulbs, micro-plasma emitters, IR blackbody sources, or the like. In addition, a sensor module may include various types of sensors including and/or in addition to optical sensors. For example, a sensor module may include one or more inertial sensors (e.g., an accelerometer, piezoelectric sensor, vibration sensor, photoreflector sensor, etc.) for detecting changes in motion, one or more thermal sensors (e.g., a thermopile, thermistor, resistor, etc.) for measuring temperature of a part of the body, one or more electrical sensors for measuring changes in electrical conduction, one or more skin humidity sensors, and/or one or more acoustical sensors.

Referring back to FIG. 1, various components of a wearable biometric monitoring device 10, according to embodiments of the present invention, are illustrated. The biometric monitoring device 10 includes one or more sensors 12 (e.g., one or more sensors in the sensor regions 24, 34 of the devices in FIGS. 2A-2B and 3A-3B, etc.), and at least one processor 14 that is coupled to the sensor(s) 12 and that is configured to receive and analyze signals produced by the sensor(s). The illustrated biometric monitoring device 10 also includes a communication component 16 and an adjustment mechanism 18.

The communication component 16 allows the processor(s) 14 to communicate with a wearer of the biometric monitoring device 10 via a remote device 40, such as a smart phone, computer, etc. In some embodiments, the communication component 16 and processor component 14 may be integrated together, such as with a wireless processor, such as a Bluetooth chipset, WiFi chipset, ZigBee chipset, or the like.

The adjustment mechanism 18 may be any type of device that facilitates proper placement of the biometric monitoring device 10 relative to the body of the subject. Exemplary adjustment mechanisms 18 may include, but are not limited to, actuators, spacers, padding, straps, ear gel devices, ear stabilization pieces (such as pieces designed to fit within regions of the ear to stabilize an earbud within the ear), adjustment holes (such as the holes used to adjust a belt or wristband on the body via a bar or wedge that fits in the holes and secures the belt or band), ratcheting mechanism(s), spring mechanisms (such as structure that compresses a part of the housing or sensor region to the body of a subject), threaded mechanisms (such as a jackscrew, etc.), fluid compression mechanisms, air pumping mechanisms, etc. In some cases, the adjustment mechanism may be autonomous and may not require physical adjustment by the subject wearing the device, for example, as described in PCT Application No. US2015/042636, which is incorporated herein by reference in its entirety.

It should be understood that the wearable device 10 may comprise all or only part of the illustrated components (i.e., sensor(s) 12, processor(s) 14, communication component(s) 16, or adjustment mechanism 18). In the case where the wearable device 10 comprises only some of these components, the functionality of the remaining components may be realized all or in part by a remote device 40. The remote device 40 may be in wired or wireless communication with the wearable device 10. Non-limiting examples of such remote devices 40 may include a smartphone or other type of phone, a sensor hub, a computer, a smart pad, a cloud-based processing system, a wearable accessory, a control box, a "medallion", a smartwatch, smart glasses, etc.

Figure 4:
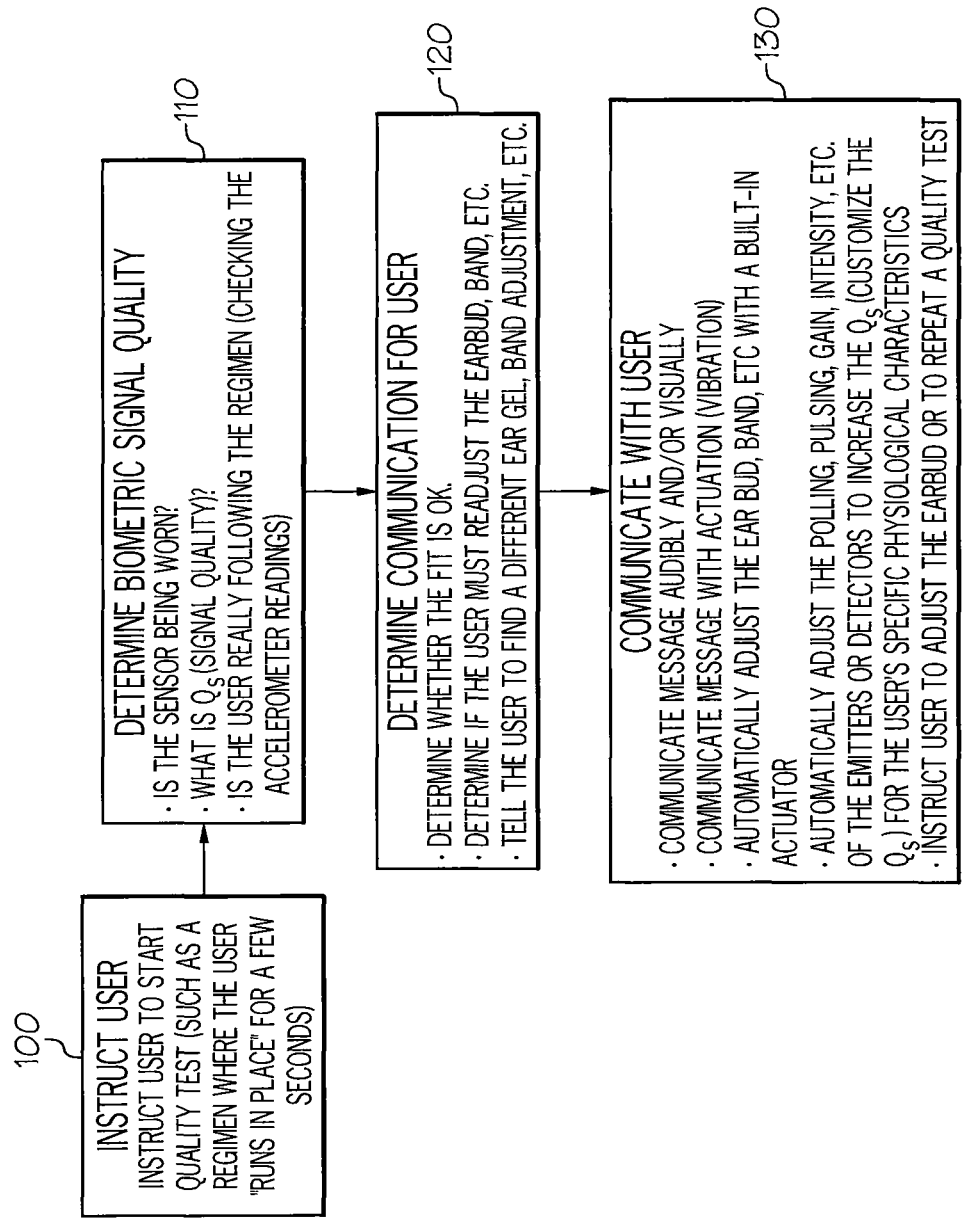
FIG. 4 is a flowchart of operations for monitoring and improving signal quality of a wearable biometric monitoring device, according to some embodiments of the present invention.

Referring now to FIG. 4, operations for adjusting signal quality of one or more sensors of a wearable biometric monitoring device 10, according to some embodiments of the present invention, are illustrated. Initially, the wearer of a biometric monitoring device 10 is instructed via the processor(s) 14 to initiate a signal quality test (Block 100). The signal quality test may involve various activities that result in motion noise. For example, the user may be instructed to run in place (or jump, dance, cycle, etc.) for a short time interval (e.g., a few seconds, etc.). The processor(s) 14 then determines the quality of the signal(s) from the sensor(s) of the biometric monitoring device 10 during the quality test regimen (Block 110). Additional operations associated with determining the signal quality may include determining if the biometric monitoring device 10 is being worn by the user and determining if the user is actually following the quality test regimen (i.e., running in place, etc.) by checking readings from one or more sensors in the device, such as a PPG sensor and/or an accelerometer associated with the biometric monitoring device 10.

Next, the processor(s) 14 determines what information to communicate to the wearer of the biometric monitoring device 10 (Block 120) and communicates this information to the user (Block 130). For example, the processor(s) determines whether the fit of the biometric monitoring device 10 is okay or whether the user needs to readjust the biometric monitoring device 10 in some way, and this information is communicated to the user. For example, if the biometric monitoring device 10 is positioned correctly (i.e., sensor signal quality is acceptable), the processor(s) 14 communicates this information to the user. If the biometric monitoring device 10 is not positioned correctly (i.e., sensor signal quality is not acceptable), the processor(s) 14 communicates this information to the user.

Information communicated to the user may be audibly and/or visually communicated. For example, FIGS. 5A-5B, 6A-6B, 7A-7B, and 8A-8B illustrate various visual communications to a user regarding whether the fit of the biometric monitoring device 10 is okay or whether the user needs to readjust the biometric monitoring device 10 in some way. These visual communications may be made to the user via the wearable biometric monitoring device 10 and/or via a remote device 40 (e.g., a smartphone, computer, etc.) in communication with the biometric monitoring device 10.

Figure 5B:
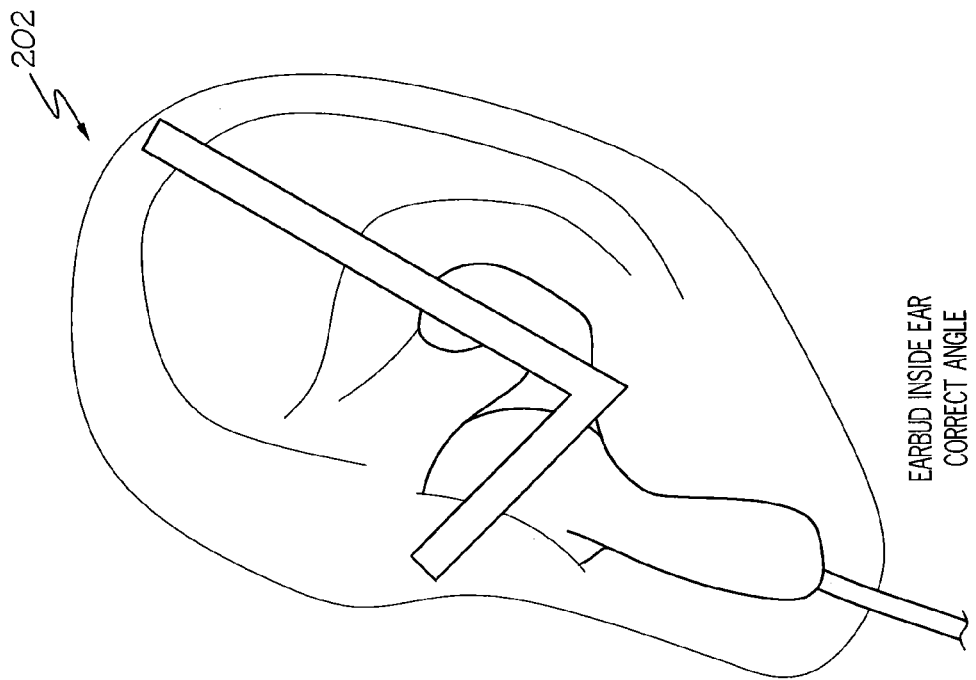
FIGS. 5A-5B, 6A-6B, 7A-7B and 8A-8B illustrate communications sent to a user in the form of graphical illustrations, and that can facilitate the proper positioning of a monitoring device, according to some embodiments of the present invention.
Figure 5A:
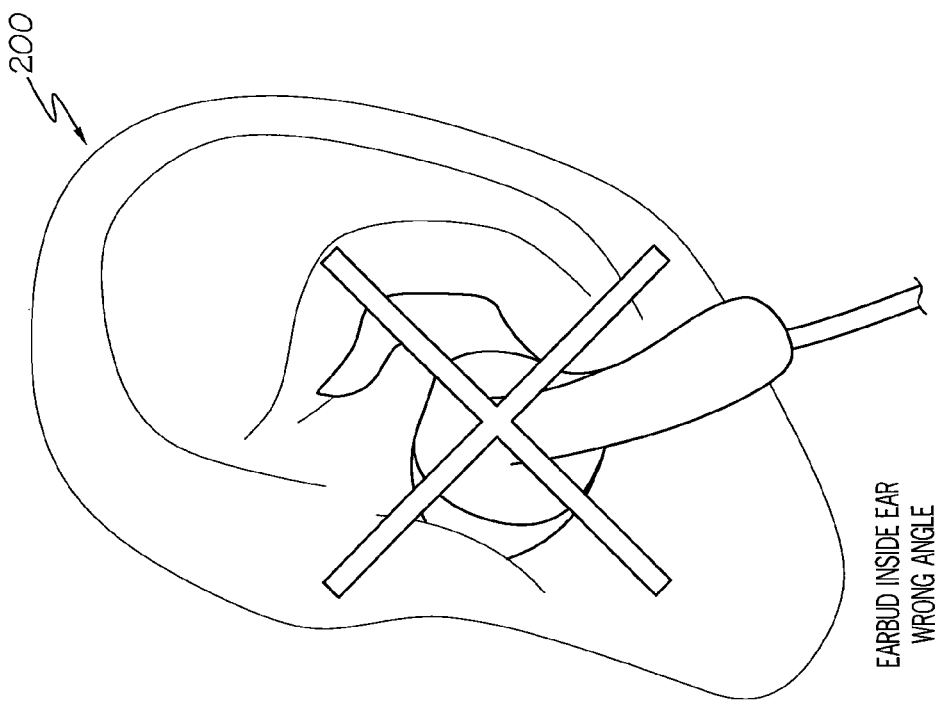

FIG. 5A illustrates a communication sent to a user in the form of a graphical illustration 200 that a biometric monitoring device 10 in the form of an earbud is positioned inside the ear of the user at an incorrect angle. FIG. 5B illustrates a communication sent to a user in the form of a graphical illustration 202 that a biometric monitoring device 10 in the form of an earbud is positioned inside the ear of the user at the correct angle.

Figure 6B:
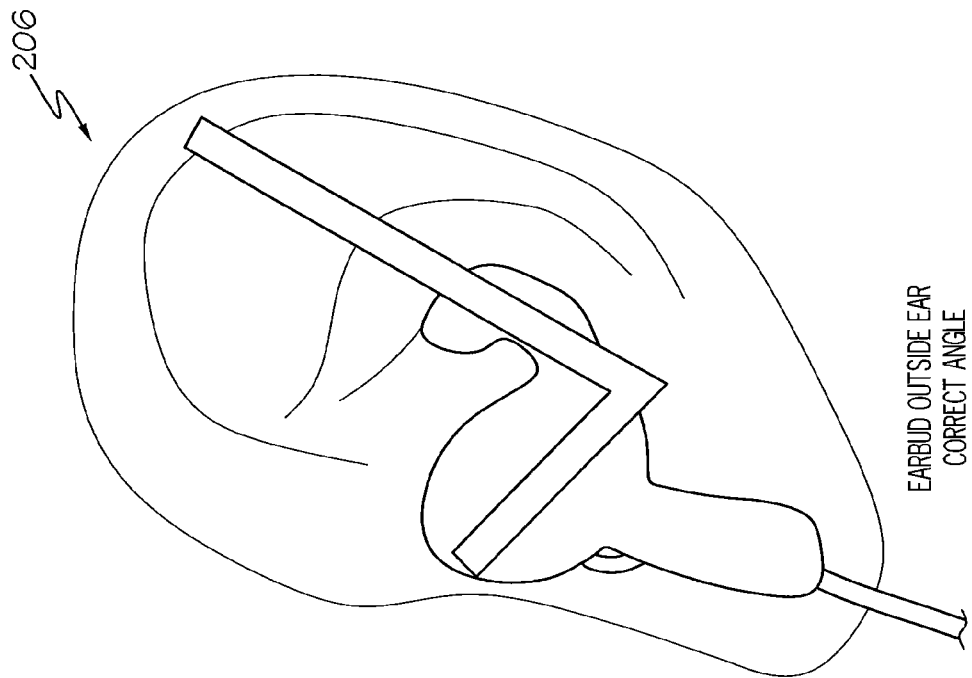
Figure 6A:
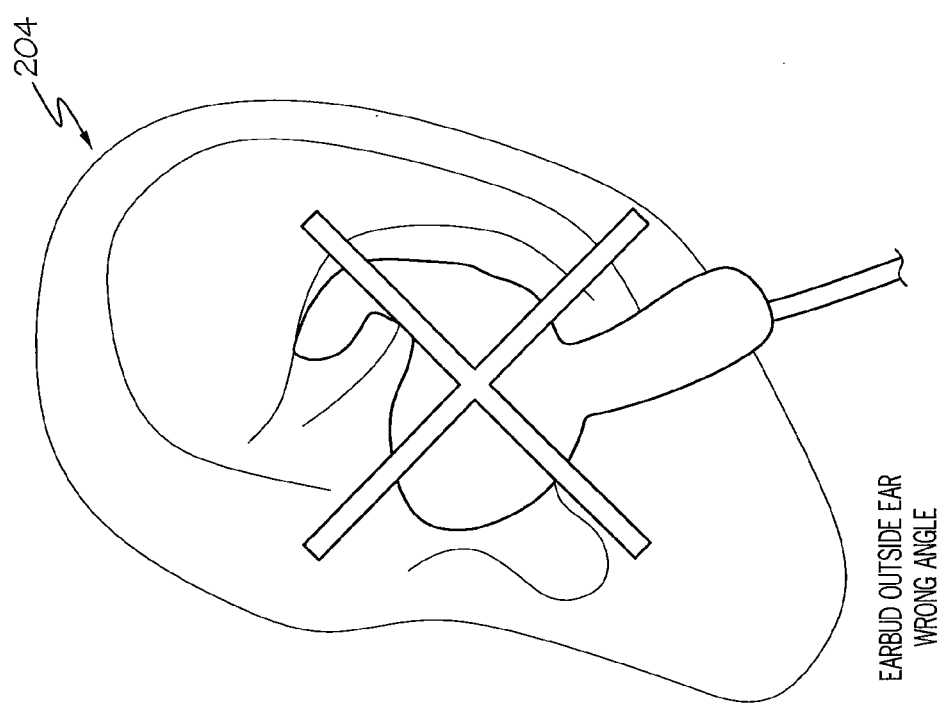

FIG. 6A illustrates a communication sent to a user in the form of a graphical illustration 204 that a biometric monitoring device 10 in the form of an earbud is positioned outside the ear of the user at an incorrect angle. FIG. 6B illustrates a communication sent to a user in the form of a graphical illustration 206 that a biometric monitoring device 10 in the form of an earbud is positioned outside the ear of the user at the correct angle.

Figure 7B:
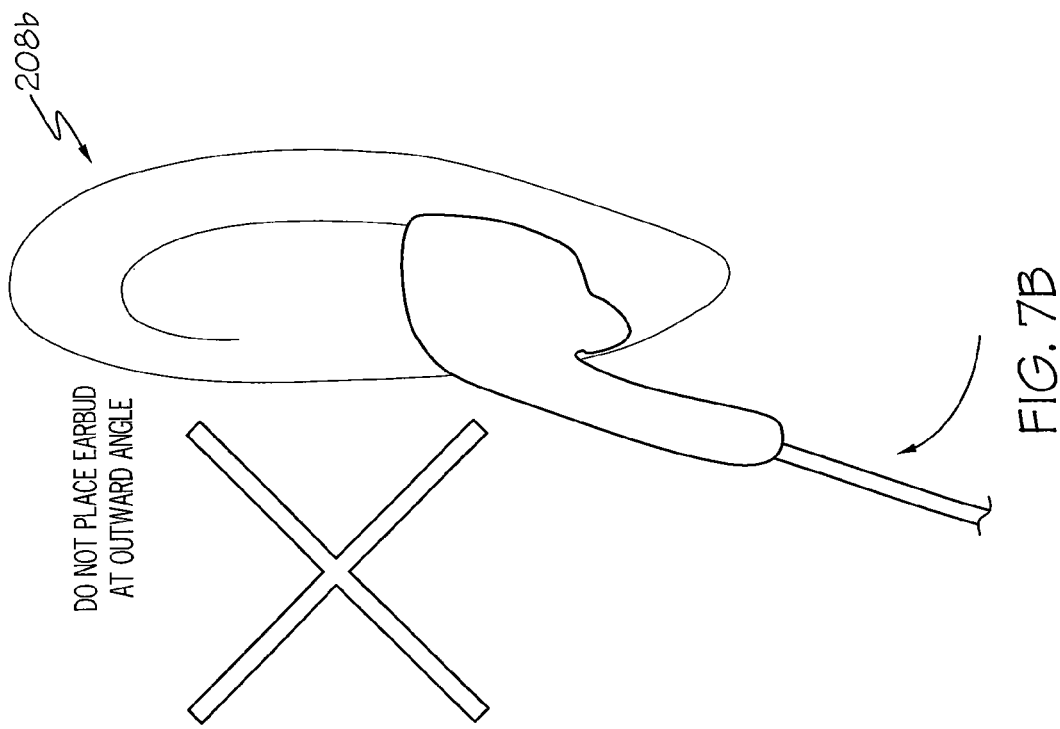
Figure 7A:
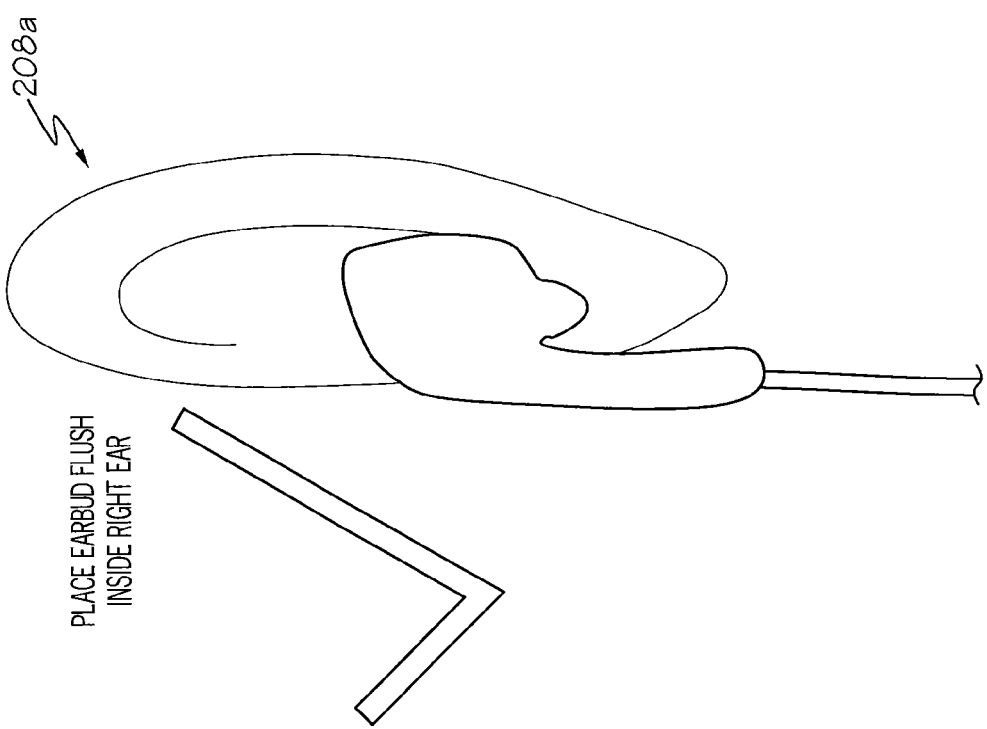

FIG. 7A illustrates a communication sent to a user in the form of a graphical illustration 208a that a biometric monitoring device 10 in the form of an earbud is positioned correctly within the ear of a user. FIG. 7B illustrates a communication sent to a user in the form of a graphical illustration 208b that a biometric monitoring device 10 in the form of an earbud is positioned at an incorrect angle within the ear of the user.

Figure 8B:
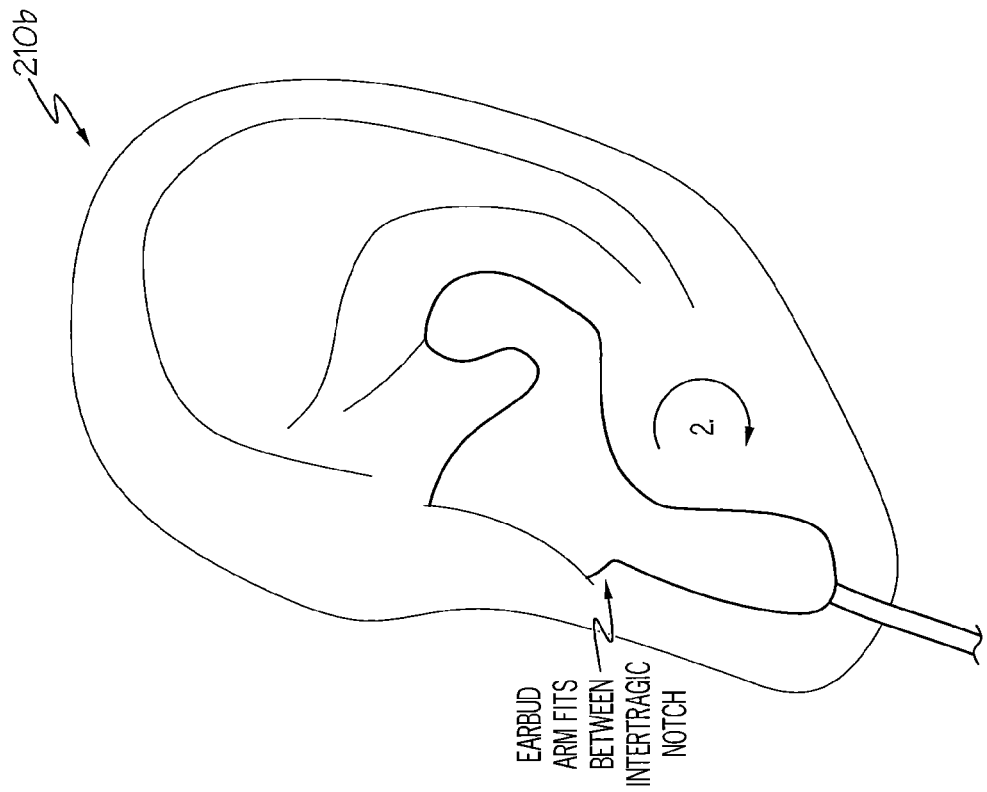
Figure 8A:
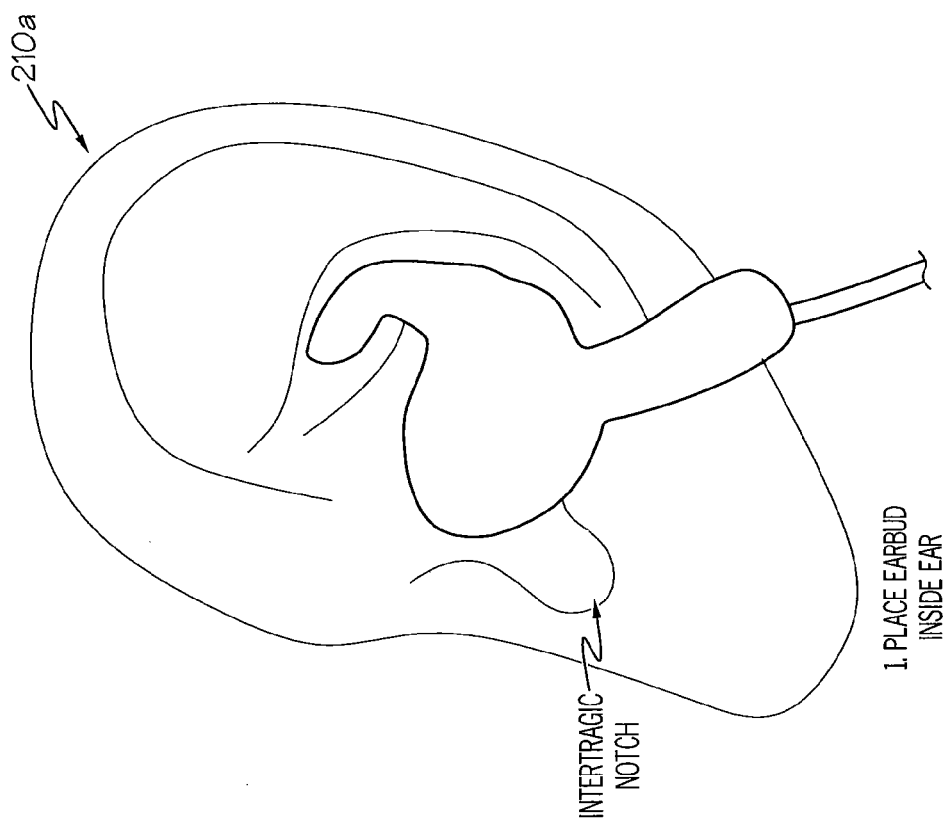

FIGS. 8A and 8B illustrate communications sent to a user in the form of graphical illustrations 210a, 210b with instructions for properly positioning a biometric monitoring device 10 in the form of an earbud within the ear of the user. For example, the graphical illustration 210a of FIG. 8A instructs the user to place the earbud inside the ear, and the graphical illustration 210b of FIG. 8B instructs the user to rotate the earbud forward such that the earbud arm fits between the intertragic notch and "locks" the sensor region of the earbud inside the ear.

The aforementioned examples of audio-visual communication to the user are illustrative only and not meant to be limiting. For example, if a PPG sensor is located at the tip of an earbud, and if the signal quality from that PPG sensor is deemed to be insufficient, the visual presentation to the user may suggest that the subject place the ear tip deeper in the ear, change the ear tip gel, rotate the tip, etc. Similarly, for the case of a band, such a wristband, comprising a PPG sensor, the visual presentation may suggest that the subject tighten the band, change the band fitting, rotate the band, etc.

Figure 9:
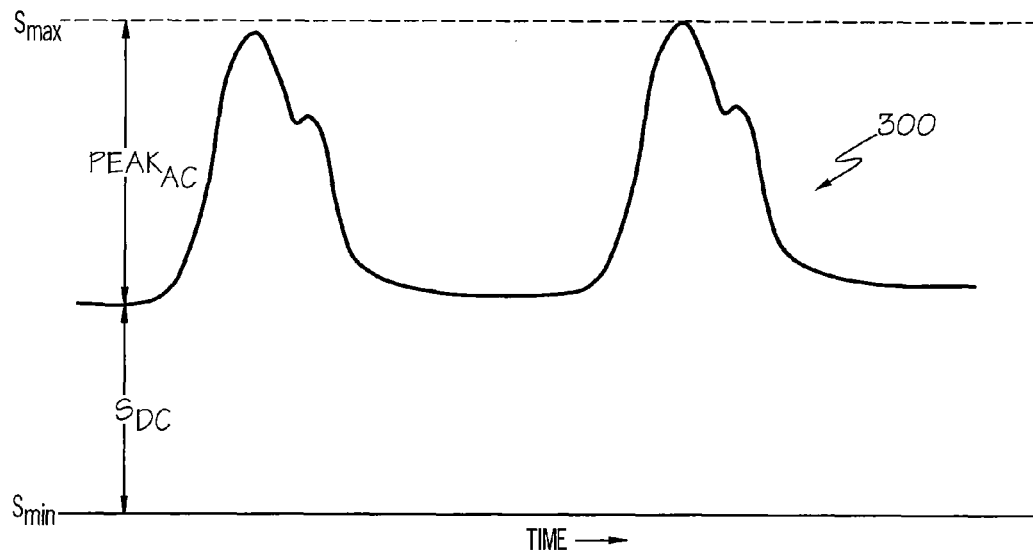
FIG. 9 is a graphical illustration of a time-domain PPG waveform produced by a wearable biometric monitoring device according to some embodiments of the present invention and where there are negligible motion artifacts associated with the waveform.
Figure 10:
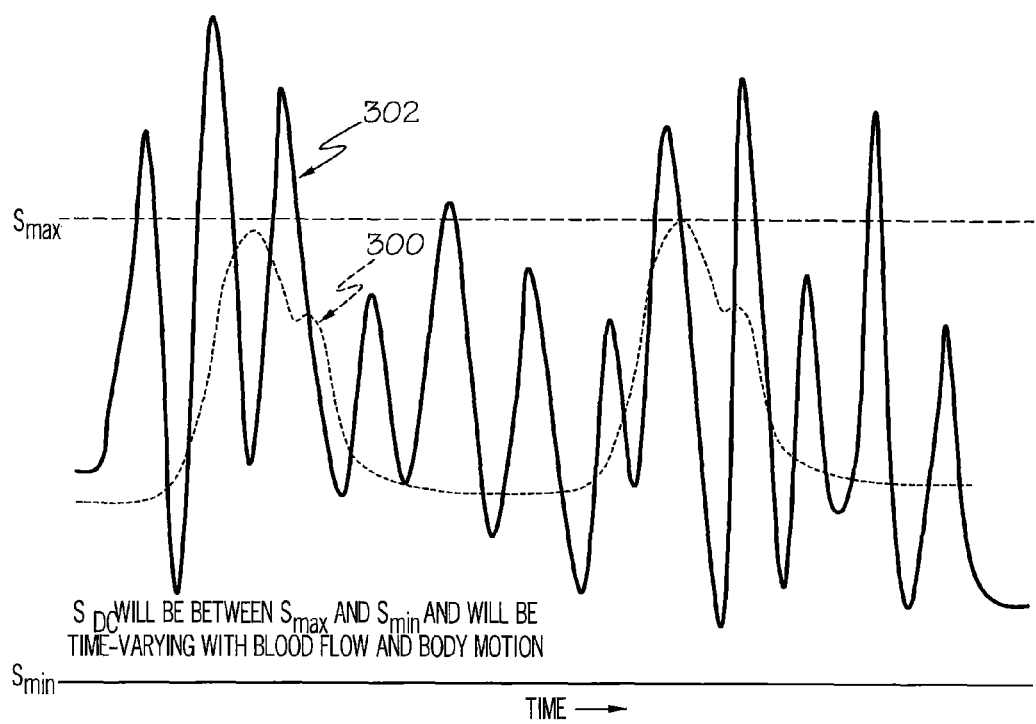
FIG. 10 is a graphical illustration of a time-domain PPG waveform produced by a wearable biometric monitoring device according to some embodiments of the present invention and where there are substantial motion artifacts associated with the waveform.

Referring now to FIG. 9, a time-domain PPG waveform 300 is illustrated. The AC component ("Peak AC") represents the pulsatile component of the photoplethysmogram, the component related to blood flow, and the DC component ($S_{DC}$) represents the non-pulsatile component. The illustrated waveform 300 is from the sensor(s) 12 within a biometric monitoring device 10 worn by a user and illustrates the condition where there are negligible motion artifacts associated with the waveform as a result of user motion, footsteps, breathing, etc. The illustrated waveform 300 illustrates two heartbeats of the user. FIG. 10 illustrates a time-domain PPG waveform 302 from the sensor(s) 12 within a biometric monitoring device 10 worn by a user where there are substantial motion artifacts. The actual heart beat waveform 300 is illustrated in dotted line and is masked by the substantial motion artifacts.

Figure 11A:
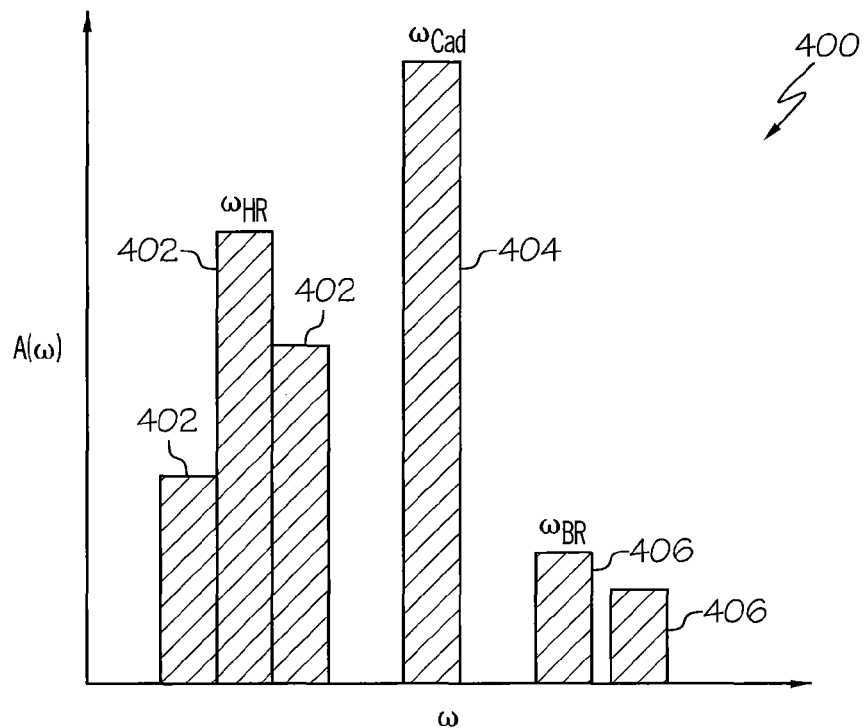
FIG. 11A illustrates an exemplary spectrogram of a PPG signal from a user wearing a biometric monitoring device having a PPG sensor according to some embodiments of the present invention and without active motion noise removal.
Figure 11B:
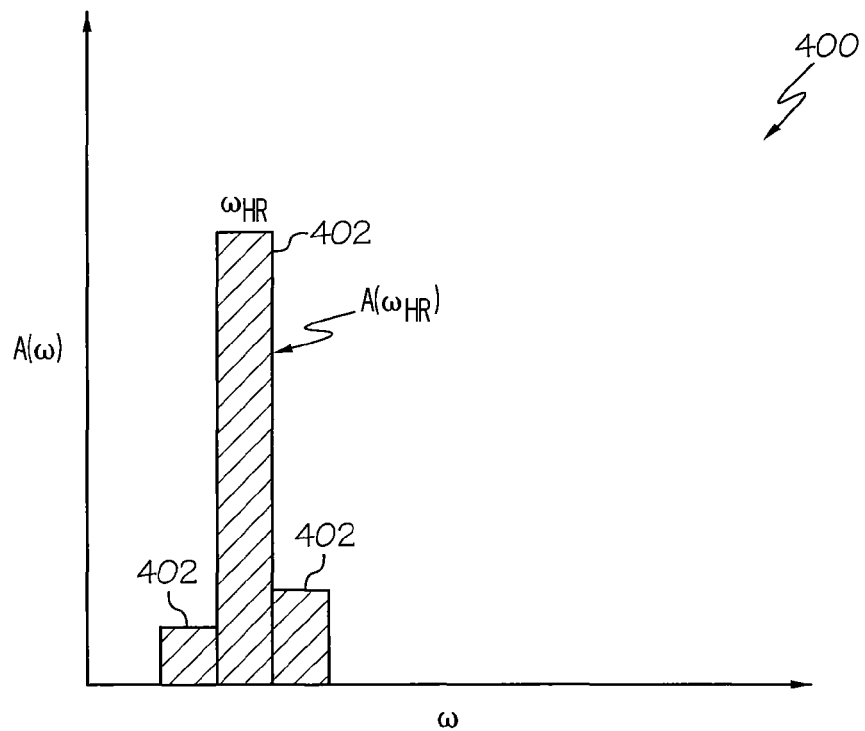
FIG. 11B illustrates the removal of motion noise from the spectrogram of FIG. 11A via one or more filters.

FIG. 11A illustrates an exemplary spectrogram 400 of a PPG signal from a user wearing a biometric monitoring device 10 and without active motion noise removal. $A(\omega)$ refers to the spectral amplitude of the PPG signal at a frequency $\omega$. The spectrogram 400 includes, not only heart rate (HR) signals 402, but also motion signals from body motion 404 and motion signals from user breathing 406. In FIG. 11B, active motion noise removal via one or more filters associated with the processor(s) 14 have removed the motion signals from body motion 404 and motion signals from user breathing 406. Noise attenuation and removal is described in detail in U.S. Pat. No. 8,157,730, U.S. Pat. No. 8,251,903, U.S. Pat. No. 8,652,040, U.S. Pat. No. 8,647,270, U.S. Pat. No. 8,700,111, U.S. Provisional Patent Application No. 61/750,490, PCT Application Publication No. WO 2013/109389, PCT Application Publication No. WO 2013/109390, and PCT Application Publication No. WO 2013/019494, which are incorporated herein by reference in their entireties.

If multiple wavelengths are used in PPG sensing, such as the case for pulse oximetry, then there will be multiple spectrograms with similar spectral profiles, and the ratio of functions of $A(\omega_{HR})_{\lambda,1}$ with respect to functions of $A(\omega_{HR})_{\lambda,2} \ldots A(\omega_{HR})_{\lambda,n}$ may be proportional to the concentration of various types of hemoglobin in the blood. For example, the $SpO_2$ concentration of blood may be proportional to $A(\omega_{HR})_{\lambda,1}/A(\omega_{HR})_{\lambda,2}$ (where $\lambda 1$ may be a shorter wavelength than $\lambda 2$) or a ratio of functions of these spectral amplitudes.

According to some embodiments of the present invention, signal quality from a sensor in the biometric monitoring device 10 can be determined by the following equation:

$$\text{Signal Quality} = Q_s \frac{\alpha(A(\omega_{HR}))}{\sum A(\omega_i)}$$

In other words, signal quality Qs is proportional to heart rate signal divided by the sum of the signal components (the sum of all spectral amplitudes for all of the "n" discrete frequencies $\omega_i$, for i=0 to n) associated with user motion. This formula may be useful once a spectrogram is generated for a PPG signal collected by the sensor(s) 12. In the spectral domain, the signal quality Qs may be expressed as a ratio of the spectral amplitude at the HR (heart rate) frequency divided by a sum of various other spectral amplitudes that may also exist in the spectrogram. Similarly, the signal quality Qs may be related to a ratio of functions of various spectral amplitudes. The signal quality Qs may be assessed either before or after motion-artifact removal, but in the case of assessing signal quality post-motion-artifact removal, the sum of spectral amplitudes in the denominator is likely to be smaller than for the case of assessing signal quality pre-motion-artifact removal, as suggested by FIG. 11A and FIG. 11B. Thus, when there are less spectral artifacts from motion artifacts and other unwanted time-varying artifacts, the signal quality Qs is likely to be higher than for the case where many such artifacts are present.

The formula for assessing signal quality is not meant to be limiting. Various other formulas or methods may be used to assess signal quality according to embodiments of the present invention. For example, a different, simpler formula may assess only the magnitude of the spectral amplitude at the HR frequency. A different, more complicated formula may assess the ratio of 2 or more signal qualities, as calculated from the above formula for multiple PPG wavelengths. Additionally, a time-domain approach may be preferred in some embodiments. For example, the peak amplitude of a time-domain photoplethysmogram (such the PeakAC as shown in FIG. 9) may be calculated and used to assess signal quality, with higher PeakAC correlating with higher Qs. In the time domain, a more complicated method may be to assess Qs by the ratio: PeakAC/PeakCadence, where Peak-Cadence refers to the peak amplitude of an accelerometer output at the user's cadence (step rate, jumping rate, cycling rate, etc.). Additionally, the spectral and time-domain approaches described above for a PPG sensor may also be applied for the case where the sensors comprise an ECG sensor (such as that used in ECG leads, ECG chest straps or ECG wristbands) and an inertial sensor (such as an accelerometer).

Embodiments of the present invention may also be applied for measuring PPG from the ear canal, body temperature from the tympanic membrane, or various other biometrics at various locations of the body. For the case of an in-ear measurement, a user may be instructed via the wearable monitor 10 and/or remote device 40 to wiggle their ear or talk while PPG or body temperature is being measured from the ear canal or tympanic membrane. The signal quality Qs may then be calculated for these activities to make certain the signal quality is above the minimum acceptable value. In contrast, a user measuring PPG and skin temperature at the leg may be instructed to stomp the leg while signal quality Qs is being assessed.

The processor(s) 14 may also determine that the position of the wearable device 10 is not sufficient for accurate biometric monitoring. For example, the processor(s) 14 may process signal readings from an accelerometer 12 to determine if the wearable device 10 is being worn correctly with respect to the ground. One methodology for determining the location of ground via an accelerometer may be to assess three (3) or more axes of the accelerometer to determine the vector of 1G of force, using commonly known trigonometric methods, and then to assess whether that vector is sufficiently aligned with a desired vector for that 1G of force. For example, it may be desired that an accelerometer placed in an earbud have ~1G of force directly along the Z-vector. If the location of the 1G of force is found by the processor(s) 14 to be close enough to the axis along the Z-vector, then the processor(s) 14 may determine that the earbud is being worn properly (FIGS. 5B, 6B, & 7A); otherwise, the processor(s) 14 may determine that the earbud is not being worn properly (FIGS. 5A, 6A, & 7B). In some cases, determining that the subject is wearing the monitoring device 10 appropriately may involve audio-visual feedback from the monitoring device 10 and/or a remote device 40. For example, a prompt may notify a user to wear a wristband with the sensor region 34 located at a certain spot along the wrist. The processor(s) 14 may then determine whether the device is being worn appropriately in accordance with the audio-visual instructions.

Figure 12:
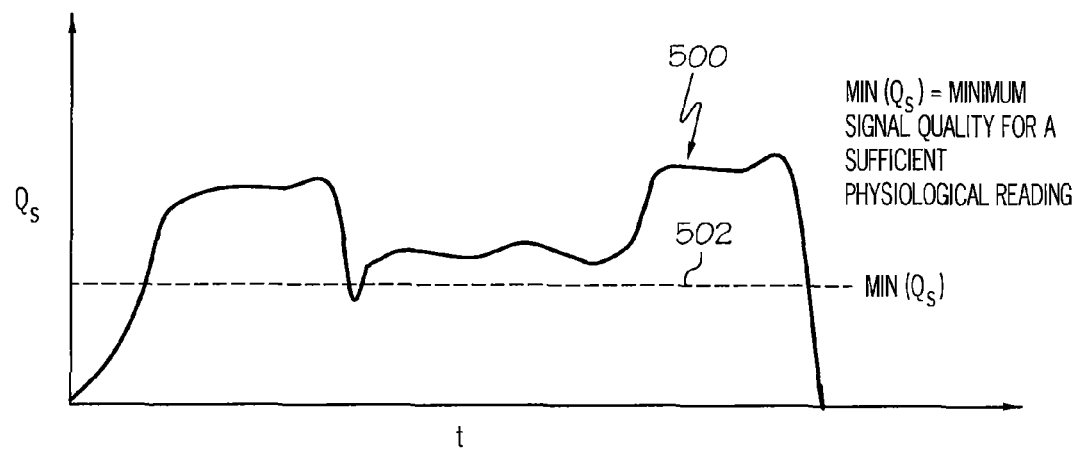
FIG. 12 is an exemplary plot of signal quality Qs from a sensor of a biometric monitoring device over time for an exemplary run by a user wearing the biometric monitoring device according to some embodiments of the present invention.

FIG. 12 is an exemplary plot 500 of signal quality Qs (as may be determined by methods described earlier as well as other methods) over time for an exemplary run by a user wearing a biometric monitoring device 10. The dotted line 502 represents the minimum signal quality Qs that is acceptable for producing accurate physiological information. The signal quality Qs may dip below the minimum acceptable quality during certain aspects of the run, such as during erratic running motion or high ambient light interference. The processor(s) 14 may determine that the signal quality Qs is too low for the measured biometric to be accurate, preventing the errant biometric reading from being applied towards a physiological assessment. For example, post analysis on the running data generated by the sensor(s) 12 in the wearable biometric monitoring device 10 may be generated by processing biometrics (heart rate, breathing rate, R-R interval, HRV, blood pressure, etc.) and activity metrics (cadence, speed, pace, distance, total steps, etc.) together. As a specific example, by processing heart rate and cadence together over time, the processor(s) 14 may determine when the user has started and stopped an exercise and may then determine the user's heart rate recovery (the change in heart rate from the stop of exercise and 1 minute or more following the stop of exercise). But, if the signal quality Qs is determined to be below the minimum allowable level of quality during the relevant data collection period (in this case the period between the stop of the exercise and a minute or more afterwards), then the processor(s) 14 may determine that heart rate recovery cannot be accurately determined. Alternatively, the processor(s) 14 may estimate the heart rate recovery with the errant data along with an assessment that the confidence of the estimation is poor, and both of the estimate and signal quality may be reported to the user audio-visually.

Figure 13:
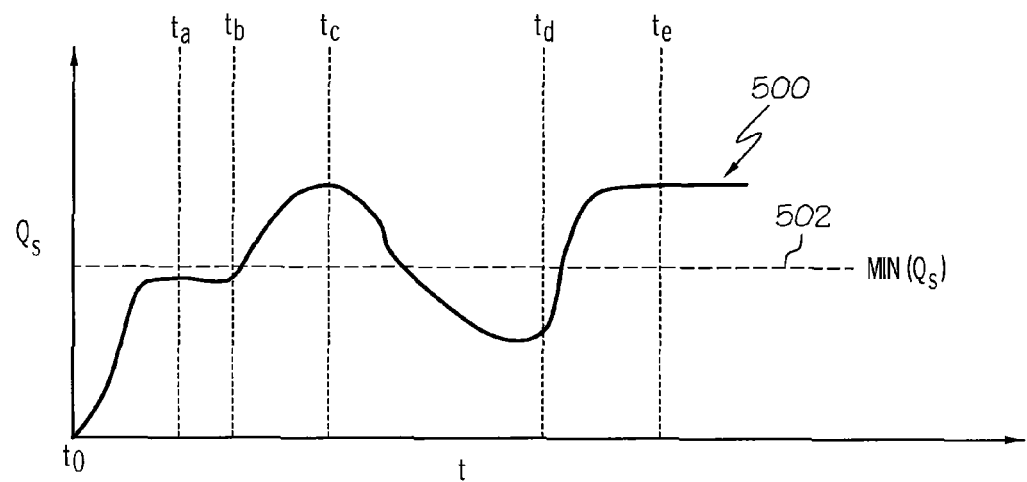
FIG. 13 is a plot of signal quality Qs from a sensor of a biometric monitoring device over time for a user conducting a self-fitting test for the biometric monitoring device, according to some embodiments of the present invention.

FIG. 13 is a plot 500 of signal quality Qs over time for a user conducting a self-fitting test, according to some embodiments of the present invention. The dotted line 502 represents the minimum signal quality Qs that is acceptable for producing accurate physiological information. The illustrated plot 500 can be presented to the user via a display in a remote device 40 in communication with the biometric monitoring device 10.

At time $t_0$, the user attaches the biometric monitoring device 10 to his/her body (e.g., inserts earbud sensor module in ear, straps on a wristband sensor module, etc.) and turns the biometric monitoring device on. At time $t_a$, the user receives the first indication of signal quality and, as illustrated, it is below the minimum signal quality line 502. At time $t_b$, the user makes one or more adjustments to the biometric monitoring device at this point to improve the signal quality. For example, the user repositions the biometric monitoring device 10 relative to the body, adds a spacer or gel device to create a better fit relative to the body, tightens a strap securing the biometric monitoring device 10 to the body, etc. As a result of the user adjustment, the signal quality improves as illustrated between time $t_b$ and time $t_c$.

However, as illustrated in FIG. 13, the user continues to adjust the biometric monitoring device 10 and the signal quality falls below the minimum signal quality line 502 by time $t_d$. The user continues adjustment of the biometric monitoring device until the signal quality is raised above the minimum signal quality line 502. At time $t_e$, the signal quality is acceptable and the user keeps the biometric monitoring device 10 in place.

Figure 14:
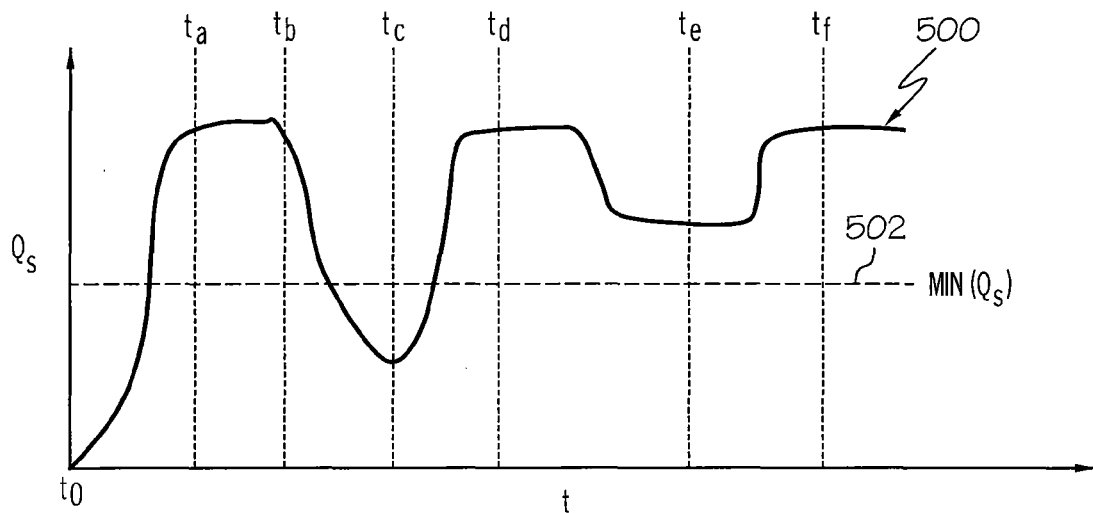
FIG. 14 is a plot of signal quality Qs from a sensor of a biometric monitoring device over time for a user conducting an instructed "quick test" regimen for the biometric monitoring device, according to some embodiments of the present invention.

FIG. 14 is a plot 500 of signal quality Qs over time for a user conducting an instructed "quick test" regimen, according to some embodiments of the present invention. The dotted line 502 represents the minimum signal quality Qs that is acceptable for producing accurate physiological information. The illustrated plot 500 can be presented to the user via a display in a remote device 40 in communication with the biometric monitoring device 10.

At time $t_0$, the user attaches the biometric monitoring device 10 to his/her body (e.g., inserts earbud sensor module in ear, straps on a wristband sensor module, etc.) and turns the biometric monitoring device on. At time $t_a$, the user is instructed to execute a "quick test" regimen, such as running in place for a short period of time (e.g., 15 seconds, etc.). As illustrated, between the time $t_a$ and $t_b$, the signal quality is above the minimum line 502, and this is because the user is at rest and motion artifacts are not impairing the signal 500. However, when the user starts the "quick test" regimen (i.e., running in place), the signal quality falls below the minimum signal quality line 502 at time $t_c$. The user is then instructed to adjust the biometric monitoring device 10 (e.g., reposition the biometric monitoring device 10 relative to the body, add a spacer or gel device to create a better fit relative to the body, tighten a strap securing the biometric monitoring device 10 to the body, etc.) and repeat the "quick test" regimen (e.g., running in place). As a result of the user adjustment, the signal quality improves as illustrated at times $t_d$ and $t_e$. The signal quality remains above the minimum signal quality line 502 at time $t_f$ after the "quick test" regimen.

Figure 15:
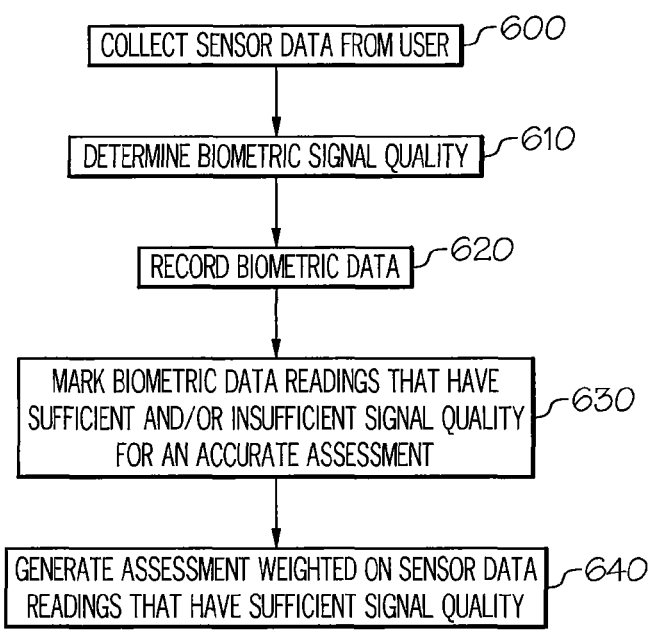
FIG. 15 is a flowchart of operations for generating biometric assessments of subjects wearing a biometric monitoring device, according to some embodiments of the present invention.
Figure 19:
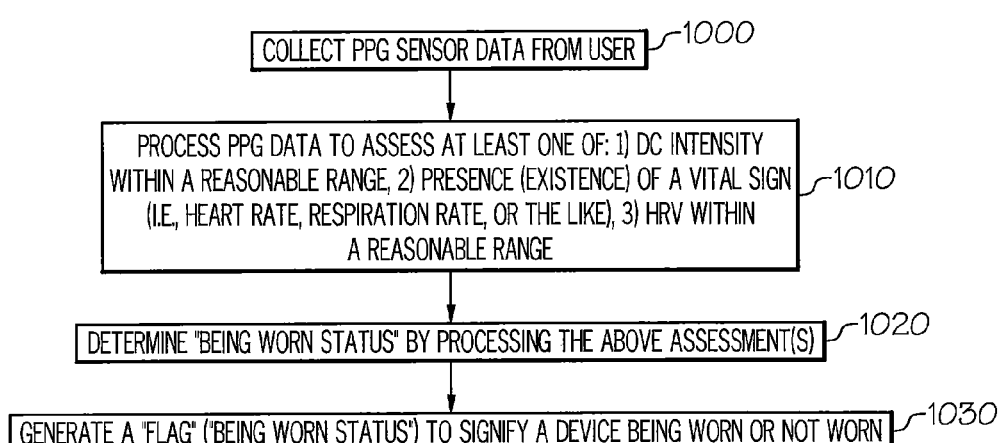
FIGS. 19-20 are flowcharts of operations for detecting that a monitoring device is being worn by a subject, according to some embodiments of the present invention.
Figure 20:
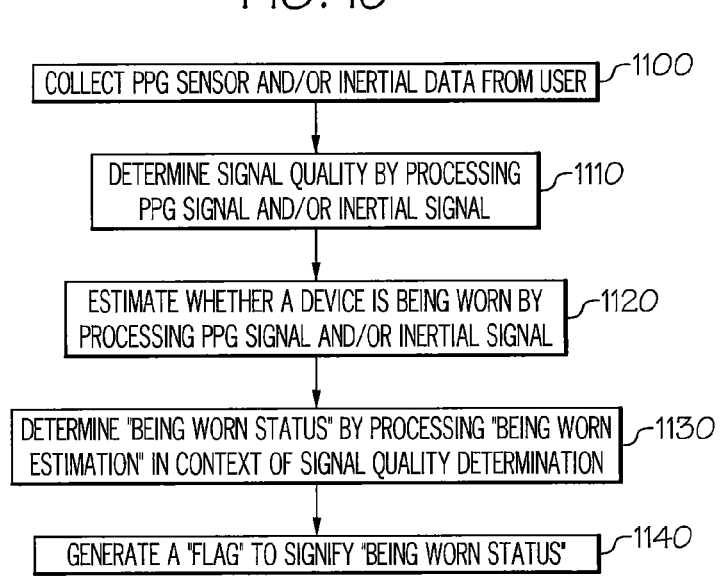

The methods described for determining the quality of a biometric signal may be applied towards facilitating accurate autonomous biometric assessments by assuring the utilization of only highly accurate data. For example, as summarized in FIG. 15, for a subject donning a wearable sensor device 10, the device 10 may collect sensor data (Block 600), determine the biometric signal quality (Block 610), record the biometric data (comprising both sensor data and biometric signal quality data) (Block 620), and then mark (i.e., label or identify) biometric data readings that have sufficient and/or insufficient quality for an accurate assessment (Block 630). Once sufficient quality data is identified and isolated from data having insufficient data quality, this quality data may be used to generate an accurate assessment for the subject (Block 640). As a specific example, a fitness assessment for the subject may be generated by assessing only those biometric data points that are found to have sufficient quality for the assessment. The biometric data that may be assessed for quality using the method of FIG. 15 may include not only vital sign biometrics (e.g., subject heart rate, subject blood pressure, subject temperature, subject respiration rate, and/or subject perspiration rate, etc.), but also contextual biometrics (biometric assessments), such as whether a person is breathing sufficiently, whether a device is being worn correctly, or the like. A specific example of applying the method illustrated in FIG. 15 towards a determination of a device "being worn" is illustrated in FIGS. 19 and 20, described below.

As another example, an accurate fitness assessment may require inputting more vetted data points into the assessment model than those that have been vetted by the wearable device 10 to be of sufficient quality. In such case, the fitness assessment may be generated by factoring both types of data points (e.g., data points having sufficient signal quality (vetted data points) and data points not having sufficient quality) by extrapolating or otherwise interpolating between data points that are marked as having sufficient data quality. A specific example of this is presented in FIG. 16 for the case of determining heart rate recovery for heart rate data having both high quality and low quality sensor signals.

Figure 16:
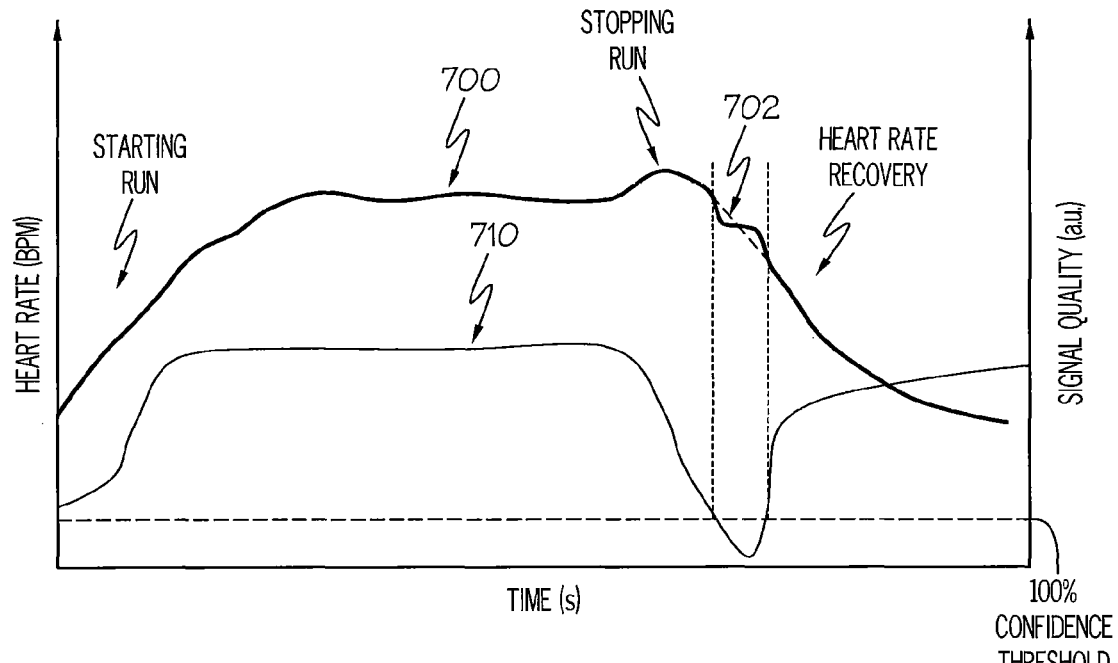
FIG. 16 illustrates heart rate data over time produced by both high quality and low quality sensor signals of a wearable biometric monitoring device.

In FIG. 16, plot 700 represents high quality sensor signals and plot 710 represents low quality sensor signals. In FIG. 16, the dotted line 702 is interpolated between two regions of high quality data, where the signal confidence is above the 100% confidence threshold. Note that for this heart rate recovery assessment to be completely autonomous, contextual information may be required to be known, such as whether the person was exercising for a sufficient period of time, if they were at an elevated heart rate or exertion level, and/or when the person stopped exercising. This type of contextual information may be input by the user via a user interface or provided by processing data from an accelerometer or other motion-tracking device that is integrated within the wearable device 10.

Figure 17:
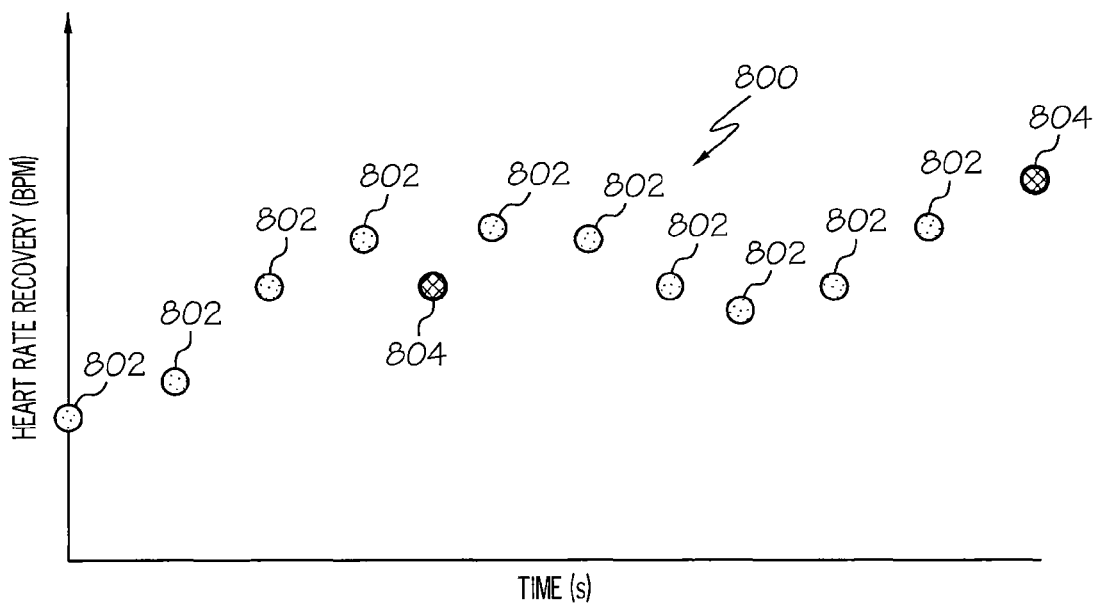
FIG. 17 is a plot of HRR (Heart Rate Recovery) over time for a user and also includes information about the confidence of HRR score for each data point.

It should also be noted that, for the example of FIG. 16, an alternative method of generating the fitness assessment may be to generate an assessment plus assessment confidence using all data points, whether they be marked as sufficient or insufficient in quality. In this case, an interpolation may not be required, as all data points are used to make the assessment but a "score" or "confidence" of the overall assessment (in this example a heart rate recovery assessment) is generated by weighting high- and low-quality data points. In a specific example of this, if 20% of the data points required to generate a fitness assessment have been found to be of insufficient signal quality, then the assessment may be calculated using 100% of the data points but with a note that the assessment confidence score is less than 100%. Additionally, if an assessment is taken over the course of time, then a notification may be given to the user when the assessment was calculated with 100% confidence and less than 100% confidence, such as the case for FIG. 17, where a plot 800 of HRR (Heart Rate Recovery) vs. time is presented for a user along with information about the confidence of that HRR score for each data point. For example, data points 802 represent 100% confidence in HRR and data points 804 represent less than 100% confidence in HRR.

The methods described for determining the quality of a biometric signal may be applied towards facilitating accurate autonomous biometric assessments by assuring the utilization of data collected only when a device 10 is being worn. For example, a wearable sensor device 10 may comprise sensors 12 that cannot innately determine if the sensor device 10 is being worn by the subject. Thus, without an intelligent way of determining that a sensor device 10 is being worn, erroneous assessments may be generated. As a specific example, a person wearing an optical heart rate monitor may find that removing the monitor from the body and placing that monitor on a counter yields erroneous heart rate readings, perhaps due to the device picking up ambient light flicker and/or scattered light from table vibrations. In such case, an assessment of that subject's average heart rate for the day, or calories burned for the day, may be wildly skewed. A method of addressing this problem is summarized in FIG. 18.

Figure 18:
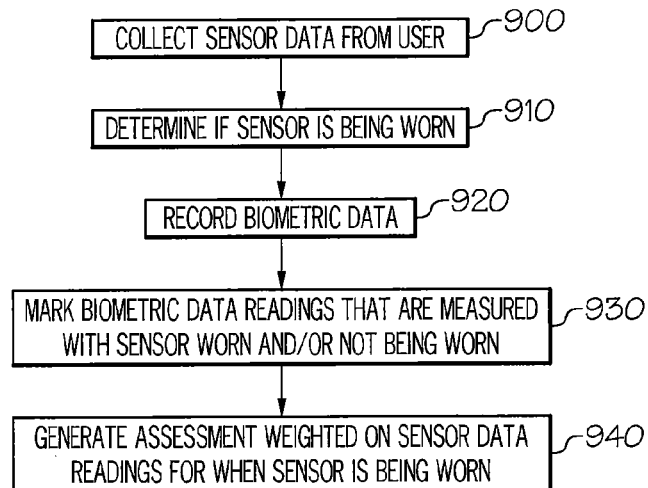
FIG. 18 is a flowchart of operations for generating biometric assessments of subjects only when a biometric monitoring device is being worn, according to some embodiments of the present invention.

In FIG. 18, a wearable device 10 having a sensor 12 may collect sensor data from a user (Block 900), determine if the sensor 12 is being worn (Block 910), and record the biometric data (comprising both sensor data and biometric signal quality data) (Block 920). The wearable device 10 may be programmed to mark when the biometric data readings are found to be associated with the device 10 not being worn (Block 930), such as the case for very low signal quality. Then an accurate assessment may be generated for the subject by factoring (weighting) sensor readings marked for periods where the wearable device 10 was determined to be worn (Block 940), as described above with respect to FIG. 16. Techniques for determining whether a device 10 is being worn by the user have been described above; however, an additional technique may comprise averaging motion signals collected by a motion sensor, such as an accelerometer, over a period of time to determine whether the average motion is high enough to be classified as "being worn" motion.

A variety of methods may be used to determine whether a device 10 is being worn. For example, the signal quality may be assessed by processing sensor readings to see if they are within an acceptable range. For example, the output of a photodetector in a wearable PPG sensor may be processed to determine if the DC (i.e., the DC component of a PPG signal) background is above or below a certain threshold associated with being worn or not worn. In many optical configurations, the DC background will be lower than a certain threshold when a PPG sensor is away from the body.

Additionally, the output of a PPG sensor may be processed by a processor for determining heart rate, breathing rate, and/or other vital sign(s) and then determining if the vital sign(s) is reasonable for a human being (in general), based on a record of normative data for humans or humans of a certain characteristic (gender, age, habitus, demographic, etc.), or if the vital sign(s) is reasonable for a given subject based on a personalized record collected for that subject.

Referring to FIG. 19, a process for detecting that a biometric monitoring device 10 is being worn by a subject is illustrated. The biometric monitoring device 10 includes a PPG sensor and the method includes collecting PPG sensor data (Block 1000), processing the PPG data (Block 1010), determining a "being worn status" using the processed PPG data (Block 1020), and generating an indicator or flag regarding the "being worn status" of the monitoring device (Block 1030). Processing the PPG data (Block 1010) may include determining if DC intensity (i.e., the intensity of the DC component of the PPG sensor signal) is within a reasonable range, determining the presence (i.e., existence) of a vital sign (subject heart rate, subject blood pressure, subject temperature, subject respiration rate, and/or subject perspiration rate, etc.), determining if heart rate value (HRV) is within a reasonable range, etc. The flag is used to indicate if the monitoring device 10 is being worn by the subject or not being worn by the subject (i.e., the "being worn status").

Referring to FIG. 20, a process for detecting that a biometric monitoring device 10 is being worn by a subject is illustrated. The biometric monitoring device 10 includes a PPG sensor and the method includes collecting PPG sensor data and/or inertial data via a motion sensor associated with the monitoring device 10 (Block 1100). The signal quality of the PPG sensor data and/or inertial data is determined via processing (Block 1110) and an estimate is made as to whether the monitoring device 10 is being worn via the processed PPG sensor data and/or inertial data (Block 1120). A "being worn status" is determined by processing the estimate as to whether the monitoring device 10 is being worn in context with the signal quality of the PPG sensor data and/or inertial data (Block 1130). An indicator or flag is then generated regarding the "being worn status" of the monitoring device (Block 1140). The flag is used to indicate if the monitoring device 10 is being worn by the subject or not being worn by the subject (i.e., "being worn status").

In another embodiment for determining if a device 10 is being worn, a PPG sensor 12, and/or a processor 14 in communication with the PPG sensor, may be configured to generate RRi (R-R interval) and or heart rate variability (HRV) information, and this information can be processed to determine if the statistics of consecutive R-R intervals (the time intervals, NN, between consecutive ECG or PPG peaks) is consistent with a living person (or not). This innovation can be particularly important for the aforementioned case where table or floor vibrations may generate a false signal in a PPG sensor, emulating heart rate. In such case, the processor may confuse consecutive peaks from optical scatter signals caused by table vibrations as a real live heart rate, and thus generate a false signal (or flag) that the device is being worn. But, by running statistics through the time intervals between consecutive peaks, the processor 14 may be able to identify human heart rate variability from inanimate (i.e., table) vibration-caused peaks in the optical scatter signal of a PPG sensor. This is because false RRi peaks (from mechanical vibrations or external optical noise) are not likely to have the same statistical distribution as that of true RRi peaks (from a human ECG or PPG signals). For example, vibration noise or flickering noise from mechanical or optical noise sources will often generate false peaks characterized by high regularity in time (higher than that of real human-caused peaks), yielding a low STDEV (standard deviation) between successive NNs. The types of statistics on consecutive time-intervals between peaks may comprise (but are not limited to): 1) SDNN (standard deviation between consecutive time-intervals (NN)), 2) pNN50 (the percentage of successive NNs that differ by more than 50 ms (milliseconds) divided by the total number of NNs during a given time period), 3) RMSSD (the "root mean square of successive differences" between adjacent NNs, 4) PSD (power spectral density) or PSD ratios for high and low frequency ranges, 5) and the like.

Similarly, the output of a temperature sensor, such as a tympanic temperature sensor or skin sensor or the like, may be processed to determine if the temperature is above or below a certain threshold associated with being worn. In this case, the processor 14 may look for a temperature reading within a reasonable range associated with human-generated heat; being inside that range may trigger a "flag" (such as a 1 or 0 bit) that the device is being worn, whereas outside that range may change the flag to not being worn. In general, such a "being worn flag" may be generated for any determination by a processor that the device is being worn (or not worn), regardless of the sensor transduction mechanism (i.e., using the method provided in FIG. 19). In some embodiments, the output of a motion sensor may also be used to determine if a wearable device 10 is being worn. For example, the output of an accelerometer may be processed to assess micro-motions associated with a human subject at rest or processed to assess larger motions associated with gross body motion. The presence of at least sufficient micro-motions may be used to generate a "flag" that the device 10 is being worn.

It should be noted that multiple of the methods described herein for assessing whether a device 10 is being worn may be used in combination in order to improve the assessment of a device 10 being worn. As a particular example of this combinational method, a processor 14 may factor both the DC intensity of a PPG signal and the HRV of the PPG signal to determine if the device 10 is being worn. More specifically, if the DC intensity from a detector output in a PPG sensor is below (or above) a DC threshold intensity, and if the HRV determined from the detector output of a PPG signal shows an HRV below (or above) an HRV threshold intensity, then the processor may determine that the device 10 is not being worn, generating a "flag". It should be noted that when the device is not being worn, the HRV assessment would be performed on PPG data that is not truly PPG data but is rather optical noise detected from a non-worn device. Nonetheless, the term "HRV" is used here to represent the statistical analysis performed on the detector output.

Because sensor readings may be slightly different for different subjects in the case of a wearable device 10 being worn/not-worn, the generation of an accurate "being worn flag" may require that the processor 14 be trained for that particular subject. For example, the subject may be asked to input, via a user interface, when they are wearing the wearable device 10 and when they are not wearing the wearable device 10. The processor 14 may then assess sensor readings to determine the unique "signature" of that subject for the device 10 being worn and/or for the device 10 being not worn. This signature may be programmed and associated with the wearable device 10 such that a more accurate determination of being worn/not worn may be generated in the future for that subject.

Example embodiments are described herein with reference to block diagrams and flow diagrams. It is understood that a block of the block diagrams and flow diagrams, and combinations of blocks in the block diagrams and flow diagrams, can be implemented by computer program instructions that are performed by one or more computer circuits, such as electrical circuits having analog and/or digital elements. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and flow diagrams, and thereby create means (functionality) and/or structure for implementing the functions/acts specified in the block diagrams and flow diagrams.

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and flow diagrams.

A tangible, non-transitory computer-readable medium may include an electronic, magnetic, optical, electromagnetic, or semiconductor data storage system, apparatus, or device. More specific examples of the computer-readable medium would include the following: a portable computer diskette, a random access memory (RAM) circuit, a read-only memory (ROM) circuit, an erasable programmable read-only memory (EPROM or Flash memory) circuit, a portable compact disc read-only memory (CD-ROM), and a portable digital video disc read-only memory (DVD/BlueRay).

The computer program instructions may also be loaded onto a computer and/or other programmable data processing apparatus to cause a series of operational steps to be performed on the computer and/or other programmable apparatus to produce a computer-implemented process such that the instructions which execute on the computer or other programmable apparatus provide steps for implementing the functions/acts specified in the block diagrams and flow diagrams. Accordingly, embodiments of the present invention may be embodied in hardware and/or in software (including firmware, resident software, micro-code, etc.) that runs on a processor such as a digital signal processor, which may collectively be referred to as "circuitry," "a module" or variants thereof.

It should also be noted that the functionality of a given block of the block diagrams and flow diagrams may be separated into multiple blocks and/or the functionality of two or more blocks of the block diagrams and flow diagrams may be at least partially integrated. Finally, other blocks may be added/inserted between the blocks that are illustrated. Moreover, although some of the diagrams include arrows on communication paths to show a primary direction of communication, it is to be understood that communication may occur in the opposite direction to the depicted arrows.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A method of monitoring signal quality of a wearable biometric monitoring device, wherein the biometric monitoring device includes at least one optical sensor configured to detect and/or measure physiological information from a subject wearing the biometric monitoring device, at least one motion sensor, and at least one processor in communication with the at least one optical sensor and the at least one motion sensor, wherein the at least one processor is configured to receive and analyze signals produced by the at least one optical sensor and the at least one motion sensor, the method comprising the following performed via the at least one processor:

processing information from the at least one optical sensor and/or the at least one motion sensor to determine if the monitoring device is being worn;

initiating a signal quality test of the at least one optical sensor in response to determining that the monitoring device is being worn, comprising:

instructing the subject to begin an exercise regimen; and processing information from the at least one optical sensor and the at least one motion sensor during the exercise regimen to determine if signal quality produced by the at least one optical sensor is acceptable, comprising calculating a ratio of physiological information to motion information in a signal from the at least one optical sensor, wherein a higher ratio of physiological information to motion information indicates a higher quality of the signal; and communicating information to the subject regarding the signal quality during the exercise regimen, the communicating comprising informing the subject that the device is being worn correctly if the signal quality is acceptable, and informing the subject that the device is not being worn correctly if the signal quality is not acceptable.

2. The method of claim 1, wherein communicating information to the subject regarding the signal quality further comprises communicating instructions to the subject to adjust the biometric monitoring device relative to the body of the subject in response to detecting that the signal quality is not acceptable.

3. The method of claim 1, wherein communicating information to the subject regarding the signal quality comprises communicating information to the subject that the signal quality is above a threshold level.

4. The method of claim 1, wherein instructing the subject to begin an exercise regimen comprises sending an audio and/or visual communication to a remote device in communication with the biometric monitoring device.

5. The method of claim 1, wherein communicating information to the subject regarding the signal quality comprises sending an audio and/or visual communication to a remote device in communication with the biometric monitoring device.

6. The method of claim 1, wherein instructing the subject to begin an exercise regimen comprises causing the biometric monitoring device and/or a remote device to vibrate.

7. The method of claim 1, wherein communicating information to the subject regarding the signal quality comprises causing the biometric monitoring device and/or a remote device to vibrate.

8. The method of claim 1, wherein the biometric monitoring device includes an actuator, and further comprising automatically adjusting the biometric monitoring device relative to the body of the subject via the actuator in response to determining that if the signal quality is not acceptable.

9. The method of claim 1, further comprising determining if the subject has begun the exercise regimen by detecting a change in subject activity via the at least one motion sensor.

10. The method of claim 1, wherein the biometric monitoring device is integrated within an earbud, an audio headset, a wrist strap, a wrist watch, an ankle bracelet, or an armband.

11. The method of claim 1, wherein the biometric monitoring device comprises a band configured to at least partially encircle a portion of a body of the subject, and wherein the portion of the body comprises a limb, a nose, an earlobe, and/or a digit.

12. The method of claim 1, further comprising determining if the subject is wearing the biometric monitoring device by determining via the at least one motion sensor if body motion over a period of time is above a threshold.

13. A method of monitoring signal quality of a wearable biometric monitoring device, wherein the biometric monitoring device includes at least one optical sensor configured to detect physiological information from a subject wearing the biometric monitoring device, at least one motion sensor configured to detect motion information from the subject, and at least one processor in communication with the at least one optical sensor and the at least one motion sensor, wherein the at least one processor is configured to receive and analyze signals produced by the at least one optical sensor and the at least one motion sensor, the method comprising:
  instructing the subject to begin an activity; and
  processing information from the at least one optical sensor and the at least one motion sensor during the activity to measure signal quality produced by the at least one optical sensor during the activity comprising calculating a ratio of physiological information to motion information in the signal of the at least one optical sensor, wherein a higher ratio of physiological information to motion information indicates a higher quality of the signal produced by the at least one optical sensor.

14. The method of claim 13, wherein the at least one optical sensor comprises a PPG sensor.

15. A method of generating a status indication that a biometric monitoring device is being worn by a subject, wherein the biometric monitoring device includes a PPG sensor, a motion sensor, and at least one processor in communication with the PPG sensor and motion sensor, the method comprising the following performed via the at least one processor:
  instructing the subject to begin an activity;
  processing information from the PPG sensor and the motion sensor during the activity to determine quality of a signal produced by the PPG sensor, comprising calculating a ratio of physiological information to motion information in the signal, wherein a higher ratio of physiological information to motion information indicates a higher quality of the signal;
  making an estimate as to whether the biometric monitoring device is being worn based on the signal quality of the PPG sensor; and
  generating a status indication that the biometric monitoring device is being worn by processing the estimate as to whether the biometric monitoring device is being worn in context with the signal quality of the PPG sensor.

16. The method of claim 15, wherein the biometric monitoring device is integrated within an earbud, an audio headset, a wrist strap, a wrist watch, an ankle bracelet, or an armband.

17. The method of claim 15, wherein the biometric monitoring device comprises a band configured to at least partially encircle a portion of a body of the subject, and wherein the portion of the body comprises a limb, a nose, an earlobe, and/or a digit.

* * * * *

UNITED STATES PATENT AND TRADEMARK OFFICE
CERTIFICATE OF CORRECTION

PATENT NO. : 9,794,653 B2
APPLICATION NO. : 14/829032
DATED : October 17, 2017
INVENTOR(S) : Aumer et al.

Page 1 of 1

It is certified that error appears in the above-identified patent and that said Letters Patent is hereby corrected as shown below:

In the Claims

Column 22, Claim 8, Line 57: Please correct "that if the signal" to read -- that the signal --

Signed and Sealed this
Twenty-fourth Day of July, 2018

Andrei Iancu
*Director of the United States Patent and Trademark Office*